US008053420B2

(12) United States Patent
Iversen et al.

(10) Patent No.: US 8,053,420 B2
(45) Date of Patent: *Nov. 8, 2011

(54) PEPTIDE CONJUGATED, INOSINE-SUBSTITUTED ANTISENSE OLIGOMER COMPOUND AND METHOD

(75) Inventors: Patrick L. Iversen, Corvallis, OR (US); Dwight D. Weller, Corvallis, OR (US); Jed N. Hassinger, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 714 days.

This patent is subject to a terminal disclaimer.

(21) Appl. No.: 12/060,135

(22) Filed: Mar. 31, 2008

(65) Prior Publication Data

US 2008/0182973 A1    Jul. 31, 2008

Related U.S. Application Data

(63) Continuation of application No. 11/136,245, filed on May 23, 2005, now abandoned.

(60) Provisional application No. 60/574,048, filed on May 24, 2004, now abandoned.

(51) Int. Cl.
    *A61K 31/70* (2006.01)
    *C07H 21/04* (2006.01)
(52) U.S. Cl. .......................... 514/44; 536/24.5
(58) Field of Classification Search .................. None
    See application file for complete search history.

(56) References Cited

U.S. PATENT DOCUMENTS

| | | | |
|---|---|---|---|
| 5,087,617 A | 2/1992 | Smith | 514/44 |
| 5,525,465 A | 6/1996 | Haralambidis et al. | |
| 5,747,641 A | 5/1998 | Frankel et al. | |
| 5,849,727 A | 12/1998 | Porter et al. | |
| 6,159,946 A | 12/2000 | Zalewski et al. | |
| 6,303,573 B1 | 10/2001 | Ruoslahti et al. | |
| 6,365,351 B1 | 4/2002 | Iversen | |
| 6,495,663 B1 | 12/2002 | Rothbard et al. | |
| 6,645,974 B2 | 11/2003 | Hutchinson et al. | |
| 7,468,418 B2 | 12/2008 | Iversen et al. | 530/300 |
| 2003/0032593 A1 | 2/2003 | Wender et al. | |
| 2003/0040466 A1 | 2/2003 | Vodyanoy et al. | |
| 2003/0045488 A1 | 3/2003 | Brown et al. | |
| 2003/0087861 A1 | 5/2003 | Iversen et al. | |
| 2003/0185788 A1 | 10/2003 | Rothbard et al. | |
| 2003/0235845 A1 | 12/2003 | Van Ommen et al. | |
| 2004/0170955 A1 | 9/2004 | Arap et al. | |
| 2005/0171026 A1 | 8/2005 | Hagiwara et al. | |
| 2006/0014712 A1 | 1/2006 | Neuman | |
| 2006/0078542 A1 | 4/2006 | Mah et al. | |
| 2006/0276425 A1 | 12/2006 | Mourich et al. | |
| 2007/0135333 A1 | 6/2007 | Geller et al. | |
| 2009/0082547 A1 | 3/2009 | Iversen et al. | 530/322 |
| 2009/0099066 A1 | 4/2009 | Moulton et al. | |

FOREIGN PATENT DOCUMENTS

| | | |
|---|---|---|
| WO | WO 94/04686 A1 | 3/1994 |
| WO | WO 00/44897 A1 | 8/2000 |
| WO | WO 00/71706 A1 | 11/2000 |
| WO | WO 01/62297 A1 | 8/2001 |
| WO | WO 03/068942 A2 | 8/2003 |

OTHER PUBLICATIONS

Abes et al., "Arginine-rich cell penetrating peptides: design, structure-activity, and applications to alter pre-mRNA splicing by steric-block oligonucleotides", *Journal of Peptide Science*, 14:455-460 (2008).
Abes et al., "Vectorization of morpholino oligomers by the (R-Ahx-R)4 peptide allows efficient splicing correction in the absence of endosomolytic agents", *Journal of Controlled Release*, 116(3):304-13 (2006).
Arora et al., "Bioavailability and efficacy of antisense morpholino oligomers targeted to c-*myc* and cytochrome P-450 3A2 following oral administration in rats", *Journal of Pharmaceutical Sciences*, 91(4):1009-1018 (2002).
Chen, C.P. et al., "A concise method for the preparation of peptide and arginine-rich peptide-conjugated antisense oligonucleotide", *Bioconjugate Chemistry*, 14:532-538 (2003).
International Search Report from PCT Application No. PCT/US2004/013660, search report dated Feb. 21, 2005, 5 pages (2005).
Eriksson, M. et al.,"Cell permeabilization and uptake of antisense peptide-peptide nucleic acid (PNA) into *Escherichia coli*", *The Journal of Biological Chemistry*, 277(9):7144-7147 (2002).
Ghosh, C. and Iversen, P., "Intracellular delivery strategies for antisense phosphorodiamidate morpholino oligomers", *Antisense & Nucleic Acid Drug Development*, 10:263-274 (2000).
Lebleu, B. et al., "Cell penetrating peptide conjugates of steric block oligonucleotides", *Advanced Drug Delivery Reviews*, 60:517-529 (2008). Marshall, N.B. et al., "Arginine-rich cell-penetrating peptides facilitate delivery of antisense oligomers into murine leukocytes and alter pre-mRNA splicing", *Journal of Immunological Methods*, 325:114-126 (2007).
Moulton, H. et al., "HIV Tat peptide enhances cellular delivery of antisense morpholino oligomers", *Antisense and Nucleic Acid Drug Development*, 13(1):31-43 (2003).
Richard, J. P. et al., "Cell-penetrating peptides. A reevaluation of the mechanism of cellular uptake", *The Journal of Biological Chemistry*, 278(1):585-590, 2003.
Rothbard, J. et al., "Arginine-rich molecular transporters for drug delivery: role of backbone spacing in cellular uptake", *J. Med. Chem.* 45:3612-3618 (2002).

(Continued)

*Primary Examiner* — Tracy Vivlemore
(74) *Attorney, Agent, or Firm* — Seed IP Law Group PLLC

(57) ABSTRACT

A therapeutic oligomer-peptide conjugate, and methods of using the conjugate are disclosed. The conjugate includes (a) a substantially uncharged oligonucleotide analog compound having a base sequence that includes a string of bases that are complementary to four or more contiguous cytosine bases in a target nucleic acid region to which the compound is intended to bind, and (b) conjugated to the compound, an arginine-rich peptide effective to enhance the uptake of the compound into target cells. The string of bases in the compound includes at least one inosine base positioned in the string so as to limit the number of contiguous guanine bases in said string to three or fewer. The conjugate has greater cellular uptake than the compound alone, by virtue of the arginine-rich peptide, and substantially greater antisense activity greater activity than the conjugate in the absence of inosine for guanine substitutions.

33 Claims, 10 Drawing Sheets

OTHER PUBLICATIONS

Stein et al., "Inhibition of Vesivirus infections in mammalian tissue culture with antisense morpholino oligomers", *Antisense Nucleic Acid Drug Dev.*, 11(5):317-325 (2001).

Wender P. et al., "The design, synthesis, and evaluation of molecules that enable or enhance cellular uptake: peptoid molecular transporters", *Proc. Natl. Acad. Sci. USA*, 97(24):13003-13008 (2000).

Wender, P. et al., "Oligocarbamate molecular transporters: design, synthesis, and biological evaluation of a new class of transporters for drug delivery", *J. Am. Chem. Soc.* 124:13382-13383, 2002.

Zubin, E. et al., "Oligonucleotide-peptide conjugates as potential antisense agents", *FEBS Letters*, 456(1):59-62 (1999).

Dapic et al., "Biophysical and biological properties of quadruplex oligodeoxyribonucleotides", 31(8):2097-2107 (2003).

Devi, G.R., "Prostate cancer: status of current treatments and emerging antisense-based therapies", *Current Opinion Therapies*, 4(2):138-148 (2002).

Hudziak et al., "Resistance of morpholino phosphorodiamidate oligomers to enzymatic degradation", *Antisense Nucleic Acid Drug Dev.*, 6:267-272 (1996).

Iversen, P.L., *Antisense Drug Tech.*, S.T. Crooke, New York, Marcel Dekker, Inc. pp. 235-238 (2001).

Kang et al., "Up-regulation of luciferase gene expression with antisense oligonucleotides: implications and applications in functional assay development", *Biochemistry*, 37(18):6235-6239 (1998).

Knapp et al., "Resistance to chemotherapeutic drugs overcome by c-Myc inhibition in a Lewis lung carcinoma murine model.", *Anti-cancer Drugs*, 14(1):39-47 (2003).

Mizutani et al., *Cancer*, 74:2546-2554 (1994).

Moulton et al., "Cellular uptake of antisense morpholino oligomers conjugated to arginine-rich peptides", *Bioconjugate Chemistry*, 15:290-299 (2004).

Shafer and Smirnov, *Biopolymers*, "Biological aspects of DNA/RNA quadruplexes", 56(3):209-27 (2000).

Stein et al., "Inhibition of Vesivirus infections in mammalian tissue culture with antisense morpholino oligomers", *Antisense Nucleic Acid Drug Dev.*, 11(5):267-272 (1996).

Summerton, J. and Weller, D., "Inhibition of Vesivirus infections in mammalian tissue culture with antisense morpholino oligomers", *Antisense Nucleic Acid Drug Dev.*, 7:187-195 (1997).

Vanin, E.F. and Ji, T.H., "Synthesis and application of cleavable photoactivable heterobifunctional reagents", *Biochemistry*, 20(24):6754-6760 (1981).

Alter et al., "Systemic delivery of morpholino oligonucleotide restores dystrophin expression bodywide and improves dystrophic pathology", *Nature Medicine*, 12(2):175-7 (2006).

Burrer et al., "Antiviral effects of antisense morpholino oligomers in murine coronavirus infection models", *Journal of Virology*, 81(11):5637-5648 (2007).

EMBL/GenBank/DDBJ database (Deshazer) May 26, 2007 Sequence CH899747. Retrieved from the Internet URL,:http://www.ebi.ac.uk/sgi-bin/emblfetch?style+html&id+CH899747> 196 pages (2007).

Gebski et al., "Morpholino antisense oligonucleotide induced dystrophin exon 23 skipping in mdx mouse muscle", *Human Molecular Genetics*, 12(15):1801-11 (2003).

Jearawiriyapaisarn, N. et al., "Sustained Dystrophin Expression Induced by Peptide-conjugated Morpholino Oligomers in the Muscles of mdx Mice.", *Mol. Therapy*, 16(9):1624-1629 (2008).

Kolonin et al., "Synchronous selection of homing peptides for multiple tissues by in vivo phage display", *The FASEB Journal*, 20(7):979-81 (2006).

Meade, B.R. and Dowdy, S.F., "Exogenous siRNA delivery using peptide transduction domains/cell penetrating peptides", *Advanced Drug Delivery Reviews*, 59(2-3):134-40 (2007).

Samoylova, T.I. and Smith, B.F., "Elucidation of muscle-binding peptides by phage display screening", *Muscle & Nerve*, 22(4):460-6 (1999).

Wu, R.P., D.S. Youngblood et al. (2007). "Cell-penetrating peptides as transporters for morpholino oligomers: effects of amino acid composition on intracellular delivery and cytotoxicity." Nucleic Acids Res. 35(15):5182-91. (Epub Aug. 1, 2007).

Youngblood et al., "Stability of cell-penetrating peptide-morpholino oligomer conjugates in human serum and in cells", Bioconjugate Chemistry, 18(1):50-60 (2007).

Astriab-Fisher et al., "Antisense Inhibition of P-glycoprotein Expression Using Peptide—Oligonucleotide Conjugates," *Biochemical Pharmacology* 60:83-90, 2000.

Astriab-Fisher et al., "Conjugates of Antisense Oligonucleotides with the Tat and Antennapedia Cell-Penetrating Peptides: Effects on Cellular Uptake, Binding to Target Sequences, and Biologic Actions," *Pharmaceutical Research* 19(6):744-754, Jun. 2002.

Yoo et al., "PAMAM Dendrimers as Delivery Agents for Antisense Oligonucleotides," *Pharmaceutical Research* 16(12):1799-1804, 1999.

Mourich et al., "Antisense Compound and Method for Selectively Killing Activated T Cells," U.S. Appl. No. 60/505,418, filed Sep. 23, 2003, 60 pages.

Written Opinion for PCT/US2004/013660, dated Feb. 21, 2005, 7 pages.

International Preliminary Report on Patentability for PCT/US2004/013660, dated Nov. 4, 2005, 8 pages.

International Search Report for PCT/US05/18213, mailed Sep. 26, 2007, 2 pages.

Written Opinion for PCT/US05/18213, mailed Sep. 26, 2007, 6 pages.

International Preliminary Report on Patentability for PCT/US05/18213, dated Oct. 23, 2007, 7 pages.

Patrick L. Iversen, "Peptide Conjugated, Inosine-Substituted Antisense Oligomer Compounds and Method," Office Action mailed Oct. 31, 2007, for U.S. Appl. No. 11/136,245, 15 pages.

Vivès et al., "TAT Peptide Internalization: Seeking the Mechanism of Entry," *Current Protein and Peptide Science* 4:125-132, 2003.

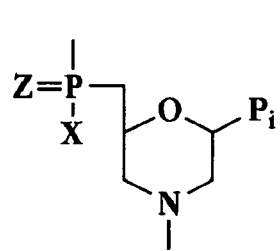
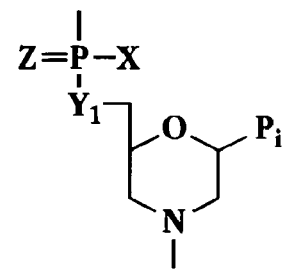
Fig. 1A          Fig. 1B
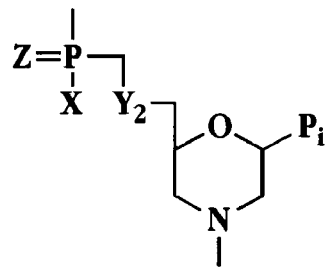
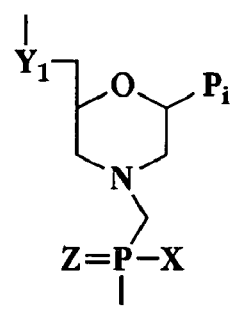
Fig. 1C          Fig. 1D

SEQUENCE LISTING

<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: Synthetic oligomer antisense to c-myc

<400> SEQUENCE: 1
acgttgaggg gcatcgtcgc    20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligomer antisense to c-myc

```
<220> FEATURE:
<221> NAME/KEY: misc_feature
<222> LOCATION: (9)..(9)
<223> OTHER INFORMATION: n = inosine

<400> SEQUENCE: 2
acgttgagng gcatcgtcgc                                                        20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (10)..(10)
<223> OTHER INFORMATION: n = inosine

<400> SEQUENCE: 3
acgttgaggn gcatcgtcgc                                                        20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (8)..(10)
<223> OTHER INFORMATION: n = inosine

<400> SEQUENCE: 4
acgttgangn gcatcgtcgc                                                        20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (8)..(11)
<223> OTHER INFORMATION: n = inosine

<400> SEQUENCE: 5
acgttgangg ncatcgtcgc                                                        20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (9)..(10)
<223> OTHER INFORMATION: n = inosine

<400> SEQUENCE: 6
acgttgagnn gcatcgtcgc                                                        20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligomer antisense to c-myc
```

```
<220> FEATURE:
<221> NAME/KEY: misc_feature
<222> LOCATION: (9)..(11)
<223> OTHER INFORMATION: n = inosine

<400> SEQUENCE: 7
acgttgagng ncatcgtcgc                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (8)..(10)
<223> OTHER INFORMATION: n = inosine

<400> SEQUENCE: 8
acgttgannn gcatcgtcgc                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (9)..(11)
<223> OTHER INFORMATION: n = inosine

<400> SEQUENCE: 9
acgttgagnn ncatcgtcgc                                                20

<210> SEQ ID NO 10
<211> LENGTH: 20
<212> TYPE: DNA
<213> ORGANISM: Artificial Sequence
<220> FEATURE:
<223> OTHER INFORMATION: synthetic oligomer antisense to c-myc
<220> FEATURE:
<221> NAME/KEY: misc_feature
<222> LOCATION: (8)..(11)
<223> OTHER INFORMATION: n = inosine

<400> SEQUENCE: 10
acgttgannn ncatcgtcgc                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligomer antisense to c-myc,
      conjugated to synthetic transport peptide
<220> FEATURE:
<221> NAME/KEY: misc_feature
<222> LOCATION: (9)..(10)
<223> OTHER INFORMATION: n = inosine
<220> FEATURE:
<221> NAME/KEY: misc_feature
<222> LOCATION: (1)..(1)
<223> OTHER INFORMATION: 5' nucleotide modified to include Arg Ahx Arg
      Arg Ahx Arg Arg Ahx Arg Arg Ahx Arg Ahx ?Ala peptide, where Ahx =
      6-aminohexanoic acid

<400> SEQUENCE: 11
acgttgagnn gcatcgtcgc                                                20
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic oligomer antisense to c-myc,
      conjugated to synthetic transport peptide
<220> FEATURE:
<221> NAME/KEY: misc_feature
<222> LOCATION: (8)..(10)
<223> OTHER INFORMATION: n = inosine
<220> FEATURE:
<221> NAME/KEY: misc_feature
<222> LOCATION: (1)..(1)
<223> OTHER INFORMATION: 5' nucleotide modified to include Arg Ahx Arg
      Arg Ahx Arg Arg Ahx Arg Arg Ahx Arg Ahx ?Ala peptide, where Ahx =
      6-aminohexanoic acid

<400> SEQUENCE: 12
acgttgannn gcatcgtcgc                                                  20

<210> SEQ ID NO 13
<211> LENGTH: 20
<212> TYPE: DNA
<213> ORGANISM: Artificial Sequence
<220> FEATURE:
<223> OTHER INFORMATION: synthetic oligomer antisense to c-myc,
      conjugated to synthetic transport peptide
<220> FEATURE:
<221> NAME/KEY: misc_feature
<222> LOCATION: (9)..(11)
<223> OTHER INFORMATION: n = a, t, g or c
<220> FEATURE:
<221> NAME/KEY: misc_feature
<222> LOCATION: (1)..(1)
<223> OTHER INFORMATION: 5' nucleotide modified to include Arg Ahx Arg
      Arg Ahx Arg Arg Ahx Arg Arg Ahx Arg Ahx ?Ala peptide, where Ahx =
      6-aminohexanoic acid

<400> SEQUENCE: 13
acgttgagnn ncatcgtcgc                                                  20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligomer antisense to c-myc,
      conjugated to synthetic transport peptide
<220> FEATURE:
<221> NAME/KEY: misc_feature
<222> LOCATION: (1)..(1)
<223> OTHER INFORMATION: 5' nucleotide modified to include Arg Ahx Arg
      Arg Ahx Arg Arg Ahx Arg Arg Ahx Arg Ahx ?Ala peptide, where Ahx =
      6-aminohexanoic acid

<400> SEQUENCE: 14
acgttgaggg gcatcgtcgc                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligomer antisense to c-myc,
      conjugated to synthetic transport peptide
<220> FEATURE:
<221> NAME/KEY: misc_feature
<222> LOCATION: (1)..(1)
<223> OTHER INFORMATION: 5' nucleotide modified to include Arg Arg Arg
      Arg Arg Arg Arg Arg Phe Phe Ahx peptide, where Ahx =
      6-aminohexanoic acid
```

```
<400> SEQUENCE: 15
acgttgaggg gcatcgtcgc                                                    20

<210> SEQ ID NO 16
<211> LENGTH: 12
<212> TYPE: PRT
<213> ORGANISM: Artificial Sequence
<220> FEATURE:
<223> OTHER INFORMATION: Synthetic transport peptide

<400> SEQUENCE: 16

Arg Arg Arg Arg Arg Arg Arg Arg Arg Phe Phe Cys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (2)..(2)
<223> OTHER INFORMATION: Xaa is Ahx, which is 6-aminohexanoic acid
<220> FEATURE:
<221> NAME/KEY: misc_feature
<222> LOCATION: (5)..(5)
<223> OTHER INFORMATION: Xaa is Ahx, which is 6-aminohexanoic acid
<220> FEATURE:
<221> NAME/KEY: misc_feature
<222> LOCATION: (8)..(8)
<223> OTHER INFORMATION: Xaa is Ahx, which is 6-aminohexanoic acid
<220> FEATURE:
<221> NAME/KEY: misc_feature
<222> LOCATION: (11)..(11)
<223> OTHER INFORMATION: Xaa is Ahx, which is 6-aminohexanoic acid

<400> SEQUENCE: 17

Arg Xaa Arg Arg Xaa Arg Arg Xaa Arg Arg Xaa Arg
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Synthetic transport peptide
<220> FEATURE:
<221> NAME/KEY: misc_feature
<222> LOCATION: (11)..(11)
<223> OTHER INFORMATION: Xaa is Ahx, which is 6-aminohexanoic acid

<400> SEQUENCE: 18

Arg Xaa Arg Xaa Arg Xaa Arg Xaa Arg Xaa Arg Xaa Arg Xaa Arg Xaa
1               5                   10                  15

<210> SEQ ID NO 19
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (1)..(1)
<223> OTHER INFORMATION: 5' modified to include peptide Arg Ahx Arg Arg
      Ahx Arg Arg Ahx Arg Arg Ahx Arg Ahx ?Ala, where Ahx =
      6-aminohexanoic acid
<220> FEATURE:
<221> NAME/KEY: misc_feature
<222> LOCATION: (10)..(10)
<223> OTHER INFORMATION: n = inosine
```

```
<400> SEQUENCE: 19
acgttgaggn gcatcgtcgc                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (1)..(1)
<223> OTHER INFORMATION: 5' modified to include peptide Arg Ahx Arg Arg
      Ahx Arg Arg Ahx Arg Arg Ahx Arg Ahx ?Ala, where Ahx =
      6-aminohexanoic acid
<220> FEATURE:
<221> NAME/KEY: misc_feature
<222> LOCATION: (8)..(10)
<223> OTHER INFORMATION: n = inosine

<400> SEQUENCE: 20
acgttgangn gcatcgtcgc                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (1)..(1)
<223> OTHER INFORMATION: 5' modified to include peptide Arg Ahx Arg Arg
      Ahx Arg Arg Ahx Arg Arg Ahx Arg Ahx ?Ala, where Ahx =
      6-aminohexanoic acid
<220> FEATURE:
<221> NAME/KEY: misc_feature
<222> LOCATION: (8)..(11)
<223> OTHER INFORMATION: n = inosine

<400> SEQUENCE: 21
acgttgangg ncatcgtcgc                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (1)..(1)
<223> OTHER INFORMATION: 5' modified to include peptide Arg Ahx Arg Arg
      Ahx Arg Arg Ahx Arg Arg Ahx Arg Ahx ?Ala, where Ahx =
      6-aminohexanoic acid
<220> FEATURE:
<221> NAME/KEY: misc_feature
<222> LOCATION: (1)..(10)
<223> OTHER INFORMATION: n = inosine

<400> SEQUENCE: 22
acgttgagnn gcatcgtcgc                                          20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
```

```
<222> LOCATION: (1)..(1)
<223> OTHER INFORMATION: 5' modified to include peptide Arg Ahx Arg Arg
      Ahx Arg Arg Ahx Arg Arg Ahx Arg Ahx ?Ala, where Ahx =
      6-aminohexanoic acid
<220> FEATURE:
<221> NAME/KEY: misc_feature
<222> LOCATION: (9)..(11)
<223> OTHER INFORMATION: n = inosine

<400> SEQUENCE: 23
acgttgagng ncatcgtcgc                                                    20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (1)..(1)
<223> OTHER INFORMATION: 5' modified to include peptide Arg Ahx Arg Arg
      Ahx Arg Arg Ahx Arg Arg Ahx Arg Ahx ?Ala, where Ahx =
      6-aminohexanoic acid
<220> FEATURE:
<221> NAME/KEY: misc_feature
<222> LOCATION: (8)..(10)
<223> OTHER INFORMATION: n = inosine

<400> SEQUENCE: 24
acgttgannn gcatcgtcgc                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (1)..(1)
<223> OTHER INFORMATION: 5' modified to include peptide Arg Ahx Arg Arg
      Ahx Arg Arg Ahx Arg Arg Ahx Arg Ahx ?Ala, where Ahx =
      6-aminohexanoic acid
<220> FEATURE:
<221> NAME/KEY: misc_feature
<222> LOCATION: (9)..(11)
<223> OTHER INFORMATION: n = inosine

<400> SEQUENCE: 25
acgttgagnn ncatcgtcgc                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (1)..(1)
<223> OTHER INFORMATION: 5' modified to include peptide Arg Ahx Arg Arg
      Ahx Arg Arg Ahx Arg Arg Ahx Arg Ahx ?Ala, where Ahx =
      6-aminohexanoic acid
<220> FEATURE:
<221> NAME/KEY: misc_feature
<222> LOCATION: (8)..(11)
<223> OTHER INFORMATION: n = inosine

<400> SEQUENCE: 26
acgttgannn ncatcgtcgc                                                    20
```

```
<210> SEQ ID NO 27
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (1)..(1)
<223> OTHER INFORMATION: 5' modified to include peptide Arg Ahx Arg Arg
      Ahx Arg Arg Ahx Arg Arg Ahx Arg Ahx ?Ala, where Ahx =
      6-aminohexanoic acid

<400> SEQUENCE: 27
acgttgaggg gcatcgtcgc                                                  20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligomer antisense to c-myc
<220> FEATURE:
<221> NAME/KEY: misc_feature
<222> LOCATION: (1)..(1)
<223> OTHER INFORMATION: 5' modified to include peptide Arg Ahx Arg Arg
      Ahx Arg Arg Ahx Arg Arg Ahx Arg Ahx ?Ala, where Ahx =
      6-aminohexanoic acid
<220> FEATURE:
<221> NAME/KEY: misc_feature
<222> LOCATION: (9)..(9)
<223> OTHER INFORMATION: n = inosine

<400> SEQUENCE: 28
acgttgagng gcatcgtcgc                                                  20

<210> SEQ ID NO 29
<211> LENGTH: 30
<212> TYPE: DNA
<213> ORGANISM: Homo sapiens

<400> SEQUENCE: 29
agcctcccgc gacgatgccc ctcaacgtta                                       30
```

PEPTIDE CONJUGATED, INOSINE-SUBSTITUTED ANTISENSE OLIGOMER COMPOUND AND METHOD

This patent application is a continuation of U.S. patent application Ser. No. 11/136,245 filed on May 23, 2005, now abandoned which in turn claims priority to U.S. Provisional Application No. 60/574,048 filed on May 24, 2004, both of which are incorporated in their entirety herein by reference.

FIELD OF THE INVENTION

This invention relates to an antisense oligomer compound (i) conjugated to an arginine rich-peptide effective to enhance the uptake of the oligomer into cells, and (ii) in which strings of G bases are broken by one of more inosine bases, and methods of using such compound.

REFERENCES

Devi, G. R. (2002). "Prostate cancer: status of current treatments and emerging antisense-based therapies." *Curr Opin Mol Ther* 4(2): 138-48.
Hudziak, R. M., E. Barofsky, et al. (1996). "Resistance of morpholino phosphorodiamidate oligomers to enzymatic degradation." *Antisense Nucleic Acid Drug Dev* 6(4): 267-72.
Iversen, P. L. (2001). Phosphoramidite Morpholino Oligomers. *Antisense Drug Technology*. S. T. Crooke. New York, Marcel Dekker, Inc.
Shafer, R. H. and I. Smirnov (2000). "Biological aspects of DNA/RNA quadruplexes." *Biopolymers* 56(3): 209-27.
Stein, D. A., D. E. Skilling, et al. (2001). "Inhibition of Vesivirus infections in mammalian tissue culture with antisense morpholino oligomers." *Antisense Nucleic Acid Drug Dev* 11(5): 317-25.
Summerton, J. and D. Weller (1997). "Morpholino antisense oligomers: design, preparation, and properties." *Antisense Nucleic Acid Drug Dev* 7(3): 187-95.
Vanin, E. F. and T. H. Ji (1981). "Synthesis and application of cleavable photoactivable heterobifunctional reagents." *Biochemistry* 20(24): 6754-60.
Dapic, V., V. Abdomerovic, et al. (2003). "Biophysical and biological properties of quadruplex oligodeoxyribonucleotides." *Nucleic Acids Res* 31(8): 2097-107.
Kang, S. H., M. J. Cho, et al. (1998). "Up-regulation of luciferase gene expression with antisense oligonucleotides: implications and applications in functional assay development." *Biochemistry* 37(18): 6235-9.
Knapp, D. C., J. E. Mata, et al. (2003). "Resistance to chemotherapeutic drugs overcome by c-Myc inhibition in a Lewis lung carcinoma murine model." *Anticancer Drugs* 14(1): 39-47.
Shafer, R. H. and 1. Smirnov (2000). "Biological aspects of DNA/RNA quadruplexes." *Biopolymers* 56(3): 209-27.
Vanin, E. F. and T. H. Ji (1981). "Synthesis and application of cleavable photoactivable heterobifunctional reagents." *Biochemistry* 20(24): 6754-60.

BACKGROUND OF THE INVENTION

Antisense oligomers offer great potential as pharmaceutical drugs, as evidenced by the number of antisense drugs currently in clinical development, and aided by the fact that a number of potential limitations of antisense oligomers have been successfully addressed over the past several years (Devi, Stein). Novel uncharged oligomer backbones have been developed to improve uptake into cells, and to increase resistance to nuclease degradation (Hudziak, Iversen, Summerton). For some oligomer structures, for example, morpholino based structures, the modified backbone has been found to give enhanced binding affinity to its target nucleic acid (Iversen, Summerton).

More recently, it has been discovered that a variety of arginine-rich peptides can dramatically increase the level of uptake of uncharged oligonucleotides into cells, including mammalian cells (see, for example, co-owned U.S. patent application Ser. No. 60/466,703, filed Apr. 29, 2003, and corresponding U.S. patent application for "Compositions for Enhancing Transport of Molecules into Cells," filed Apr. 29, 2004, both of which are incorporated herein in its entirety). This discovery has the potential to significantly increase the therapeutic potential of a variety of antisense oligomers, including those intended to block expression of selected proteins, those aimed at blocking certain donor or acceptor splice sites in pre-processed mRNA, and those designed to treat viral infection by blocking expression of viral genes or replication of single-stranded viral genomes.

In some antisense applications, the optimal targeting sequence against which the oligomer antisense is directed may include a run of four of more cytosine bases, in which case the oligomer will contain a corresponding string of four or more complementary guanine bases. As an important example, an optimal target sequence for the c-myc protein is a region containing the AUG start site of the c-myc RNA that includes a run of four cytosine bases. Anti-sense oligomers directed against the start-codon region of c-myc have a number of important therapeutic applications, including the treatment of cancer, polycystic kidney disease (see, for example, co-owned U.S. Pat. No. 6,875,747, which is incorporated herein in its entirety), coronary-vessel restenosis (see, for example, co-owned PCT patent application WO00/44897, published Aug. 3, 2000, which is incorporated herein in its entirety), and cancer therapy (see, for example, co-owned U.S. patent application US-2003-0087861-A1, published May 8, 2003, which is incorporated herein by reference in its entirety.)

Surprisingly, it has now been found that conjugating an arginine-rich peptide to antisense compounds having runs of four or more guanine bases, in an effort to enhance the cellular uptake of the oligomer, severely compromises the antisense activity of the compound, as well as the ability to purify the compound. Although the basis of this problem is not understood, it appears to involve an interaction between the positively charged peptide and the oligomer compound in a way that promotes formation of G-quartets in the oligomer, thus reducing the solubility and/or ability of the compound to bind to its target nucleic acid. It would therefore be useful to enhance the cellular uptake of such antisense oligomer compounds, by conjugating the compound with an arginine-rich peptide, without degrading the antisense activity of the compound with respect to its intracellular target.

In particular, it would be useful to enhance the cellular uptake of the above c-myc antisense compound without loss of antisense activity, for purposes of enhancing the compound's therapeutic activity in the treatment of cancer, polycystic kidney disease or coronary-vessel restenosis.

SUMMARY OF THE INVENTION

The method includes, in one aspect, an improvement in a method for enhancing the cellular uptake of a substantially uncharged oligonucleotide analog compound, by forming a conjugate of the compound and an arginine-rich peptide effective to enhance the uptake of the compound into target cells, where the compound includes a string of bases that are complementary to four or more contiguous cytosine bases in a target nucleic acid region to which the compound is intended to bind. The improvement includes substituting an inosine base for at least one guanine base in the string of bases in the compound so as to limit the number of contiguous guanine bases in the string to three or fewer, preferably two or fewer.

The improvement may be effective to enhance the water solubility of the conjugate during a purification step involving conjugate binding to and release from a cationic ion exchange resin, relative to the same conjugate in the absence of the inosine substitution. Where the target nucleic acid region includes the start codon in an mRNA, the improvement may be effective to enhance the ability of the conjugate to block translation of the protein encoded by the mRNA, relative to the same conjugate in the absence of the inosine substitution. Where the target nucleic acid region includes a donor or acceptor splice site in an preprocessed mRNA, the improvement may be effective to enhance the ability of the conjugate to mask mRNA splicing at the target region, relative to the same conjugate in the absence of the inosine substitution.

Where the target nucleic acid region includes a virally-encoded cis-acting element involved in viral replication, the improvement may be effective to enhance the ability of the conjugate to block viral replication, relative to the same conjugate in the absence of the inosine substitution.

In an exemplary embodiment, the arginine-rich peptide comprises 8 to 16 subunits selected from X subunits, Y subunits, and optional Z subunits, including at least six X subunits, at least two Y subunits, and at most three Z subunits, where >50% of said subunits are X subunits, and where (a) each X subunit independently represents arginine or an arginine analog, said analog being a cationic α-amino acid comprising a side chain of the structure $R^1N=C(NH_2)R^2$, where $R^1$ is H or R; $R^2$ is $R^2$, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y subunit independently represents a neutral amino acid $-C(O)-(CHR)_n-NH-$, where (i) n is 2 to 7 and each R is independently H or methyl, or (ii) n is 1 and R is a neutral side chain selected from substituted or unsubstituted alkyl, alkenyl, alkynyl, aryl, and aralkyl, wherein said neutral side chain, when selected from substituted alkyl, alkenyl, and alkynyl, includes at most one heteroatom for every four carbon atoms; and (c) each Z subunit independently represents an amino acid selected from alanine, asparagine, cysteine, glutamine, glycine, histidine, lysine, methionine, serine, and threonine.

Also in an exemplary embodiment, the oligonucleotide compound is a morpholino oligomer composed of morpholino subunits linked by phosphorus-containing linkages between the morpholino nitrogen of one subunit and an exocyclic carbon at the morpholino 3-position of an adjacent subunit. The morpholino subunits may be joined by uncharged phosphorodiamidate linkages, in accordance with the structure:

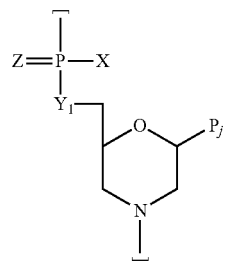

where $Y_1=O$, $Z=O$, Pj is a purine or pyrimidine base-pairing moiety effective to bind, by base-specific hydrogen bonding, to a base in a polynucleotide, and X is alkyl, alkoxy, thioalkoxy, or alkyl amino.

In another aspect, the invention includes a therapeutic oligomer-peptide conjugate composed of (a) a substantially uncharged oligonucleotide analog compound having a base sequence that includes a string of bases that are complementary to four or more contiguous cytosine bases in a target nucleic acid region to which the compound is intended to bind, and (b) conjugated to the compound, an arginine-rich peptide effective to enhance the uptake of the compound into target cells. The string of bases in the compound includes at least one inosine base, positioned in the string so as to limit the number of contiguous guanine bases in said string to three or fewer, preferably two or fewer. Exemplary embodiments of the conjugate are as described above.

In particular, for use in blocking translation of a c-myc protein, by binding to a region including the AUG start site of human c-myc mRNA, the compound's targeting sequence may include one of the sequences identified as SEQ ID NOS: 2-10. The arginine-rich peptide conjugated to the compound may include the sequence identified as SEQ ID NOS: 16, 17 or 18.

Also disclosed is a method of treating a subject having a pathological condition responsive to inhibition of c-myc expression in subject target cells. In practicing the method, a conjugate of the type just described is administered to the subject, in a therapeutically effective amount. The conjugate has greater cellular uptake than the antisense compound alone, in the absence of the arginine-rich peptide, and is more active in blocking c-myc translation than the same conjugate in the absence of the one or more inosine bases. Exemplary embodiment of the conjugate used in the method is as described above.

For use in treating bladder cancer, the conjugate may be administered by transurethral delivery, and the method may further include administering a cis-platin anti-cancer compound to the patient.

For use in reducing the risk of coronary-artery restenosis at the site of vascular injury following an angioplasty procedure, the conjugate may be delivered by intravascular delivery, for example, via a drug-releasing stent or via intravenous injection of microbubbles carrying the drug.

For use in protecting a saphenous vein placed during a coronary bypass operation, the conjugate may be administered by exposing the vein to the conjugate prior to its surgical placement.

For use in treating polycystic kidney disease, the conjugate may be administered to the subject by oral or parenteral administration.

These and other objects and features of the invention will become more fully apparent when the following detailed description of the invention is read in conjunction with the accompanying drawings.

BRIEF DESCRIPTION OF THE FIGURES

FIGS. 1A-1D show several preferred morpholino-type subunits having 5-atom (A), six-atom (B) and seven-atom (C-D) linking groups suitable for forming polymers;

FIG. 4C shows preparation of an in vivo cleavable conjugate and FIG. 4D shows preparation of a conjugate with a 6-aminohexanoic acid/beta-alanine linker;

DETAILED DESCRIPTION OF THE INVENTION

I. Definitions

Figure 2A:
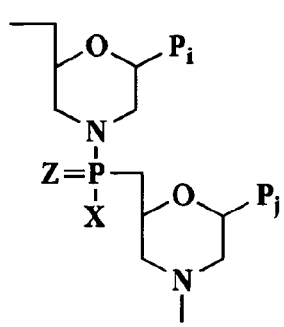
FIGS. 2A-D show the repeating subunit segment of exemplary morpholino oligonucleotides, constructed using subunits A-D, respectively, of FIG. 1.

"Alkyl" refers to a fully saturated monovalent radical containing carbon and hydrogen, which may be branched, linear, or cyclic (cycloalkyl). Examples of alkyl groups are methyl, ethyl, n-butyl, t-butyl, n-heptyl, isopropyl, cyclopropyl, cyclopentyl, ethylcyclopentyl, and cyclohexyl. Generally preferred are alkyl groups having one to six carbon atoms, referred to as "lower alkyl", and exemplified by methyl, ethyl, n-butyl, i-butyl, t-butyl, isoamyl, n-pentyl, and isopentyl. In one embodiment, lower alkyl refers to $C_1$ to $C_4$ alkyl.

"Alkenyl" refers to an unsaturated monovalent radical containing carbon and hydrogen, which may be branched, linear, or cyclic. The alkenyl group may be monounsaturated or polyunsaturated. Generally preferred are alkenyl groups having one to six carbon atoms, referred to as "lower alkenyl".

"Aryl" refers to a substituted or unsubstituted monovalent aromatic radical, generally having a single ring (e.g., benzene) or two condensed rings (e.g., naphthyl). This term includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group is replaced with a halide such as fluorine, chlorine, or bromine; with a lower alkyl group containing one or two carbon atoms; nitro, amino, methylamino, dimethylamino, methoxy, halomethoxy, halomethyl, or halo-ethyl. Preferred substituents include halogen, methyl, ethyl, and methoxy. Generally preferred are aryl groups having a single ring.

"Aralkyl" refers to an alkyl, preferably lower ($C_1$-$C_4$, more preferably $C_1$-$C_2$) alkyl, substituent which is further substituted with an aryl group; examples are benzyl (—$CH_2C_6H_5$) and phenethyl (—$CH_2CH_2C_6H_5$).

A "heterocycle" refers to a non-aromatic ring, preferably a 5- to 7-membered ring, whose ring atoms are selected from the group consisting of carbon, nitrogen, oxygen and sulfur. Preferably, the ring atoms include 3 to 6 carbon atoms. Such heterocycles include, for example, pyrrolidine, piperidine, piperazine, and morpholine.

The term "substituted", with respect to an alkyl, alkenyl, alkynyl, aryl, aralkyl, or alkaryl group, refers to replacement of a hydrogen atom with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic.

An antisense oligomer compound" or "antisense oligomer analog" or antisense compound" or oligomer analog compound" all refer to a substantially uncharged nucleic acid analog, typically having a length between 8 and 40 bases, and having a base sequence that is complementary or substantially complementary to a single-stranded target nucleic acid, e.g., a processed or preprocessed mRNA transcript, or a single-stranded viral genomic RNA or DNA. The compound may be in an unconjugated or conjugated form, e.g., conjugated to an arginine-rich peptide.

A "morpholino oligomer" is an oligonucleotide analog composed of morpholino subunit structures of the form shown in FIG. 1, where (i) the structures are linked together by phosphorus-containing linkages, one to three atoms long, preferably two atoms long, and preferably uncharged, joining the morpholino nitrogen of one subunit to the 5' exocyclic carbon of an adjacent subunit, and (ii) $P_i$ and $P_j$ are purine or pyrimidine base-pairing moieties effective to bind, by base-specific hydrogen bonding, to a base in a polynucleotide. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685; 5,217,866; 5,142,047; 5,034,506; 5,166,315; 5,521,063; and 5,506,337, all of which are incorporated herein by reference.

Figure 2B:
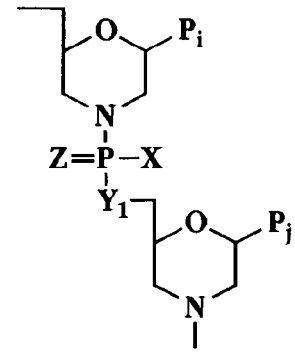
Figure 2C:
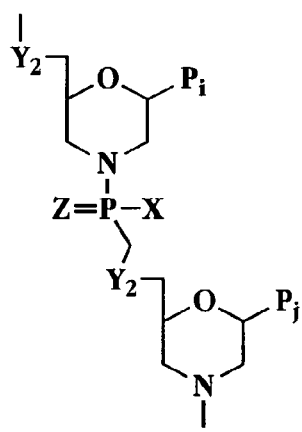
Figure 2D:
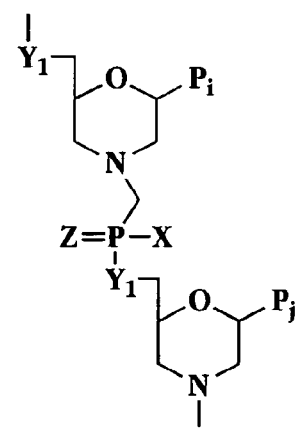

The subunit shown FIG. 1B, having a two-atom linkage, is used for 6-atom repeating-unit backbones, as shown in FIG. 2B. In these structures, the atom $Y_1$ linking the 5' morpholino carbon to the phosphorus group may be sulfur, nitrogen, carbon or, preferably, oxygen. The X moiety pendant from the phosphorus is any stable group which does not interfere with base-specific hydrogen bonding. Preferred groups include alkyl, alkoxy, thioalkoxy, and alkyl amino, including cyclic amines, all of which can be variously substituted, as long as base-specific bonding is not disrupted. Alkyl, alkoxy and thioalkoxy preferably include 1-6 carbon atoms. Alkyl amino preferably refers to lower alkyl ($C_1$ to $C_6$) substitution, and the cyclic amines are preferably 5- to 7-membered nitrogen heterocycles optionally containing 1-2 additional heteroatoms selected from oxygen, nitrogen, and sulfur. Z is sulfur or oxygen, and is preferably oxygen.

A preferred morpholino oligomer is a phosphorodiamidate-linked morpholino oligomer, referred to herein as a PMO. Such oligomers are composed of morpholino subunit structures of the form shown in FIG. 2B, where the structures are linked together by phosphorodiamidate linkages, where X=$NH_2$, NHR, or $NR_2$ (where R is lower alkyl, preferably methyl), Y=O, and Z=O, joining the morpholino nitrogen of one subunit to the 5' exocyclic carbon of an adjacent subunit, $P_i$ and $P_j$ are purine or pyrimidine base-pairing moieties effective to bind, by base-specific hydrogen bonding, to a base in a polynucleotide. Also preferred are structures having an alternate phosphorodiamidate linkage, where, in FIG. 2B, X=lower alkoxy, such as methoxy or ethoxy, Y=NH or NR, where R is lower alkyl, and Z=O.

Desirable chemical properties of the morpholino-based oligomers include the ability to selectively hybridize with a complementary-base target nucleic acid, including target RNA, with high Tm, even with oligomers as short as 8-14 bases, the ability to be actively transported into mammalian cells, and the ability of an oligomer:RNA heteroduplex to resist RNAse degradation.

A "substantially uncharged" morpholino oligomer includes at most one charged intersubunit linkage for every four, preferably for every ten, and more preferably for every twenty, uncharged intersubunit linkages. Any charged linkages are preferably charged phosphoramidate (or thiophosphoramidate) linkages, e.g. a linkage as shown in FIG. 2B where X is $O^-$ or $S^-$. Preferably, the morpholino oligomers are fully uncharged.

An "amino acid subunit" is preferably an α-amino acid residue (i.e. —CO—CHR—NH—); it may also be a β- or other amino acid residue (e.g. —CO—CH$_2$CHR—NH—), where R is a side chain.

A "G-quartet" consists of stacked planar hydrogen-bonded guanine tetramers that can cause guanine-rich nucleic acids to adopt intermolecular and intramolecular quadruplex structures that are stabilized by the presence of the G-quartets.

The term "non-natural amino acids" refers to those amino acids not present in proteins found in nature such as beta-alanine (β-Ala) or 6-aminohexanoic acid (Ahx).

II. Compound-Transporter Conjugates

The present invention includes, in one aspect, a therapeutic oligomer-peptide conjugate composed of a substantially uncharged oligonucleotide analog compound and, conjugated thereto, an arginine-rich peptide effective to enhance the uptake of the compound into target cells. The compound contains a string of bases that are complementary to four or more contiguous cytosine bases in a target nucleic acid region to which the compound is intended to bind, and this string includes at least one inosine base, positioned in the string so as to limit the number of contiguous guanine bases in the string to three or fewer. Preferably the string of bases includes at least two inosine bases, and the number of contiguous guanines in the string is two or fewer.

As will be seen below, the inosine base(s), which are complementary to the target cytosine bases, but form a less stable Watson-Crick base pair than the usual G-C base pair, serve to enhance the solubility of the conjugate during a purification step involving conjugate binding to and release from an cationic ion exchange resin, relative to the same conjugate in the absence of the inosine substitution. This enhancement is important in obtaining a purified conjugate by practical purification methods. According to another feature of the invention, the inosine-base substitution(s) are also effective to enhance the activity of the compound with respect to its target nucleic acid, as evidenced by:

(i) where the target nucleic acid region includes the start codon in an mRNA, the substitution(s) are effective to enhance the ability of the conjugate to block translation of the protein encoded by the mRNA;

(ii) where the target nucleic acid region includes a donor or acceptor splice site in an preprocessed mRNA, the substitution(s) are effective to enhance the ability of the conjugate to mask mRNA splicing at said target region; and (iii), where the target nucleic acid region includes a virally-encoded cis-acting element involved in viral replication, the substitution(s) are effective to enhance the ability of the conjugate to block viral replication, relative to the same conjugate in the absence of the inosine substitution.

Methods for demonstrating the enhanced antisense activity of the inosine-base substituted oligomer-peptide conjugates are typically cell-free translation assays and tissue culture-based assays designed to measure the inhibition of mRNA translation, preprocessed mRNA splice accuracy or viral replication.

Cell-free translation assays consist of a translation competent cell lysate (e.g., rabbit reticulocyte lysate) and input mRNA containing a reporter gene such as firefly luciferase with antisense oligomer target sequences placed immediately upstream. A variety of plasmid constructs can be used to generate the reporter mRNA. Antisense oligomers are added to the cell-free translation reaction and the relative inhibition of the reporter gene signal is a measure of the antisense activity. More detailed descriptions of cell-free translation assays used to describe the present invention are presented in Examples 4 and 5.

Tissue culture-based assays designed to demonstrate inhibition of mRNA translation use antisense oligomers targeted to either native cellular genes whose translation products (e.g. proteins) can be quantitatively measured or reporter genes that have been stably transfected into a cell line. Measurement of the degree of translation inhibition of the target mRNA can be performed using a variety of analytical methods including reporter gene signal output or quantitation of protein expression using immunological methods.

Inhibition of preprocessed mRNA splicing can be demonstrated by measuring the level of mis-spliced mRNA by northern blots or quantitative polymerase chain reaction in cells treated with antisense oligomers targeted to splice donor or acceptor sites. An alternative approach (see e.g. (Kang, Cho et al. 1998) utilizes a cell line stably transfected with a plasmid that has a luciferase gene interrupted by a mutated human beta-globin intron that causes incorrect splicing. Antisense oligomers targeted to the mutation within the intron results in splice correction and up-regulation of functional luciferase reporter protein.

Enhanced activity of antisense oligomers targeted to cis-acting elements involved in viral replication can be demonstrated using standard tissue culture-based viral replication assays or viral replicons. Inhibition of viral replication in the presence of antisense oligomers is measured by determining the titer of virus that has replicated in the presence of the antisense oligomer. Viral replicon systems utilize derivatives of full length infectious viral clones where the viral structural genes have been replaced either in part or completely with a reporter gene. The replicons are introduced, usually by transfection, into cells that are infected with replication competent virus. The replicons encode the essential cis-acting replication elements that are recognized by the replication machinery of the virus resulting in amplification of the reporter gene and an increase in the reporter signal, e.g. luciferase activity.

A. Arginine-Rich Polypeptide Moiety

Figure 3A:
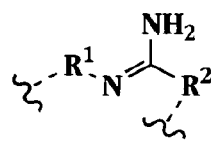
FIGS. 3A-G show exemplary X side chain structures, for use in various embodiments of the arginine-rich peptides employed in the invention.
Figure 3B:
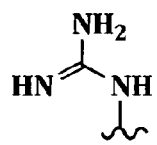
Figure 3C:
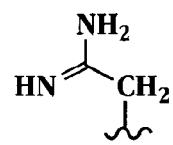
Figure 3D:
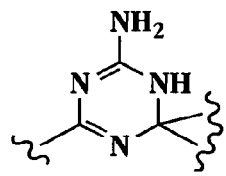
Figure 3E:
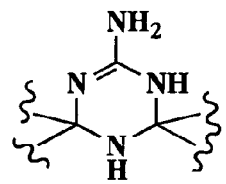
Figure 3F:
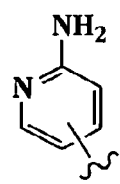
Figure 3G:
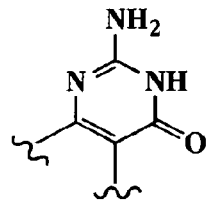

The arginine-rich peptide used in the invention for enhancing the uptake of a substantially uncharged antisense oligomer compound across a biological membrane generally comprises a moiety consisting of 10-15 subunits selected from X and Y, including 8-13 X subunits, 2-4 contiguous Y subunits, Y subunits interspersed singly amidst the X subunits, and an optional linker subunit to which the agent is linked. X represents an amino acid subunit comprising a side chain moiety of the structure $R^1N=C(NH_2)R^2$ (see FIG. 3A), where $R^1$ is H or R; $R^2$ is R, $NH_2$, NHR, or $NR_2$, where R is lower alkyl or lower alkenyl and may further include oxygen or nitrogen; $R^1$ and R² may together form a ring; and the side chain moiety is linked to the amino acid subunit via R¹ or R².

In selected embodiments, for each X, the side chain moiety is independently selected from the group consisting of guanidyl (HN=C(NH₂)NH—), amidinyl (HN=C(NH₂)C<), 2-aminodihydropyrimidyl, 2-aminotetrahydropyrimidyl, 2-aminopyridinyl, and 2-aminopyrimidonyl (FIGS. 3B-G, respectively, with possible linkage sites indicated). Note that, in structures 3D, 3E, and 3G, linking of the side chain to the amino acid subunit could take place via any of the ring —NH— groups as well as via any of the carbon atoms indicated. In one embodiment, the side chain moiety is guanidyl, as in the amino acid subunit arginine (Arg).

Y represents a hydrophobic amino acid subunit having a side chain selected from the group consisting of alkyl, alkenyl, alkynyl, aryl, aralkyl, and alkaryl, any of which may be substituted or unsubstituted; when the side chain is selected from substituted alkyl, substituted alkenyl, and substituted alkynyl, it includes at most one heteroatom for every six carbon atoms. In selected embodiments, Y represents a hydrophobic amino acid subunit having a side chain selected from the group consisting of substituted or unsubstituted aryl, aralkyl, and alkaryl. In other embodiments, each Y is selected from the group consisting of phenylalanine, tyrosine, leucine, isoleucine, and valine. In one preferred embodiment, each Y is a phenylalanine (Phe or F) subunit. In another preferred embodiment the Y subunit is the non-natural amino acid 6-aminohexanoic acid (Ahx). The X and Y subunits may be referred to herein as "cationic subunits" and "hydrophobic subunits".

As noted above, the Y subunits are either contiguous, in that no X subunits intervene between Y subunits, or interspersed singly between X subunits. However, the linking subunit may be between Y subunits. In one embodiment, the Y subunits are at a terminus of the transporter; in other embodiments, they are flanked by X subunits.

Preferably, the transporter is a peptide, where the amino acids are joined by peptide linkages. The amino acids may be d-amino acids, 1-amino acids, non-natural amino acids or a combination thereof. The compound to be delivered may be a compound employed for detection, such as a fluorescent compound, but it is preferably a biologically active agent, e.g. a therapeutic or diagnostic agent. Such agents include nucleic acids or nucleic acid analogs, particularly antisense oligonucleotides.

As demonstrated herein, the transport moieties as described above greatly enhance cell entry of attached uncharged oligomer compounds, relative to uptake of the compound in the absence of the attached transport moiety, and relative to uptake by an attached transport moiety lacking the hydrophobic subunits Y. Such enhanced uptake is preferably evidenced by at least a two-fold increase, and preferably a four-fold increase, in the uptake of the compound into mammalian cells relative to uptake of the agent by an attached transport moiety lacking the hydrophobic subunits Y. Uptake is preferably enhanced at least twenty fold, and more preferably forty fold, relative to the unconjugated compound.

A further benefit of the transport moiety is its expected ability to stabilize a duplex between an antisense oligomer and its target nucleic acid sequence, presumably by virtue of electrostatic interaction between the positively charged transport moiety and the negatively charged nucleic acid. The number of charged subunits in the transporter is less than 14, as noted above, and preferably between 8 and 11, since too high a number of charged subunits may lead to a reduction in sequence specificity.

The transport moiety also lowers the effective concentration of an antisense oligomer to achieve antisense activity as measured in both tissue culture and cell-free systems. Cell-free translation systems provide an independent means to assess the enhanced effect of the transport moiety on the antisense oligomer's ability to bind to its target and, through steric blocking, inhibit translation of downstream sequences. Cell-free translation assays designed to test the antisense activity of arginine-rich peptide-PMO conjugates demonstrate between 10 fold and 500 fold improvement in antisense activity compared to the unconjugated PMO (see Example 5 and FIGS. 6 and 7).

B. Oligomer Antisense Compound

As noted above, in one embodiment, the antisense oligomer compound is a synthetic oligomer capable of base-specific binding to a target sequence of a polynucleotide, e.g. an antisense oligonucleotide analog. Such analogs, in which the backbone structure, ring structure, or, less frequently, base structure of natural polynucleotides is modified, are well known and include charged analogs, such as phosphorothioate-linked oligonucleotides, and uncharged analogs, such as methylphosphonates and peptide nucleic acids. Some analogs, such as N3'→P5' phosphoramidates, may be charged or uncharged, depending on the substation on the linking moiety.

In a preferred embodiment, the polymer is a morpholino oligomer, as defined above, which is about 8-40 subunits in length. More typically, the oligomer is about 10-30, or about 12-25, subunits in length. For some applications, such as antibacterial, short oligomers, e.g. from about 8-12 subunits in length, can be especially advantageous, particularly when attached to a peptide transporter as disclosed herein. Preferably, the oligomer is an uncharged phosphorodiamidate-linked morpholino oligomer (PMO), also defined above. The PMO can be of any sequence, where the supported base pairing groups include standard or modified A, T, C, G, I and U bases.

According to one aspect of the invention, the target nucleic acid sequence against which the oligomer compound is directed includes a region of four or more contiguous cytosine bases. This target region may be part of the AUG start site in an mRNA, where it is desired to inhibit or block expression of a selected protein encoded by the mRNA. Alternatively, it may include or be adjacent to a donor or acceptor splice site in a preprocessed mRNA, where it is desired to block correct splicing at that site, either for purposes of creating splice mutation polypeptides, or incomplete or inactive peptides. In still another embodiment, the target may be a cis-acting element in a viral genome, where binding of the oligomer (which may be targeted against either the + or − viral genome strand), is effective to block viral replication in virus-infected cells.

Exemplary target sequences containing a string of four or more guanine bases in each of these three target types can be found from public sequence databases well know to those of skill in the Art. One exemplary target sequence described below includes the AUG start site in the human c-myc mRNA. It will be appreciated, however, that this sequence, and the various inosine for guanine substitutions made in the targeting oligomer compound are illustrative of how the oligomer compound may be modified, when targeting any target sequence with a string of four or more cytosine bases, to achieve the advantages of the invention.

The transporter can be linked to the compound to be delivered by a variety of methods available to one of skill in the art. Exemplary methods are provided in Example 1 below and illustrated in FIGS. 4A-D. In one of these examples, the transporter is a peptide containing a single cysteine residue whose side chain thiol is used for linking. The linkage point can be at various locations along the transporter. In selected embodiments, it is at a terminus of the transporter. Typically, it is adjacent to the hydrophobic residues of the transporter. Multiple transporters can be attached to a single compound if desired.

The linker can also be any combination of two β-Ala and/or Ahx residues attached to the 5' end of the PMO and the C-terminus of the peptide transporter. A preferred embodiment is to attach the Ahx residue to the C terminus of the peptide transporter and the β-Ala residue to the 5' terminus of the PMO as shown in FIG. 4D.

Figure 4A:
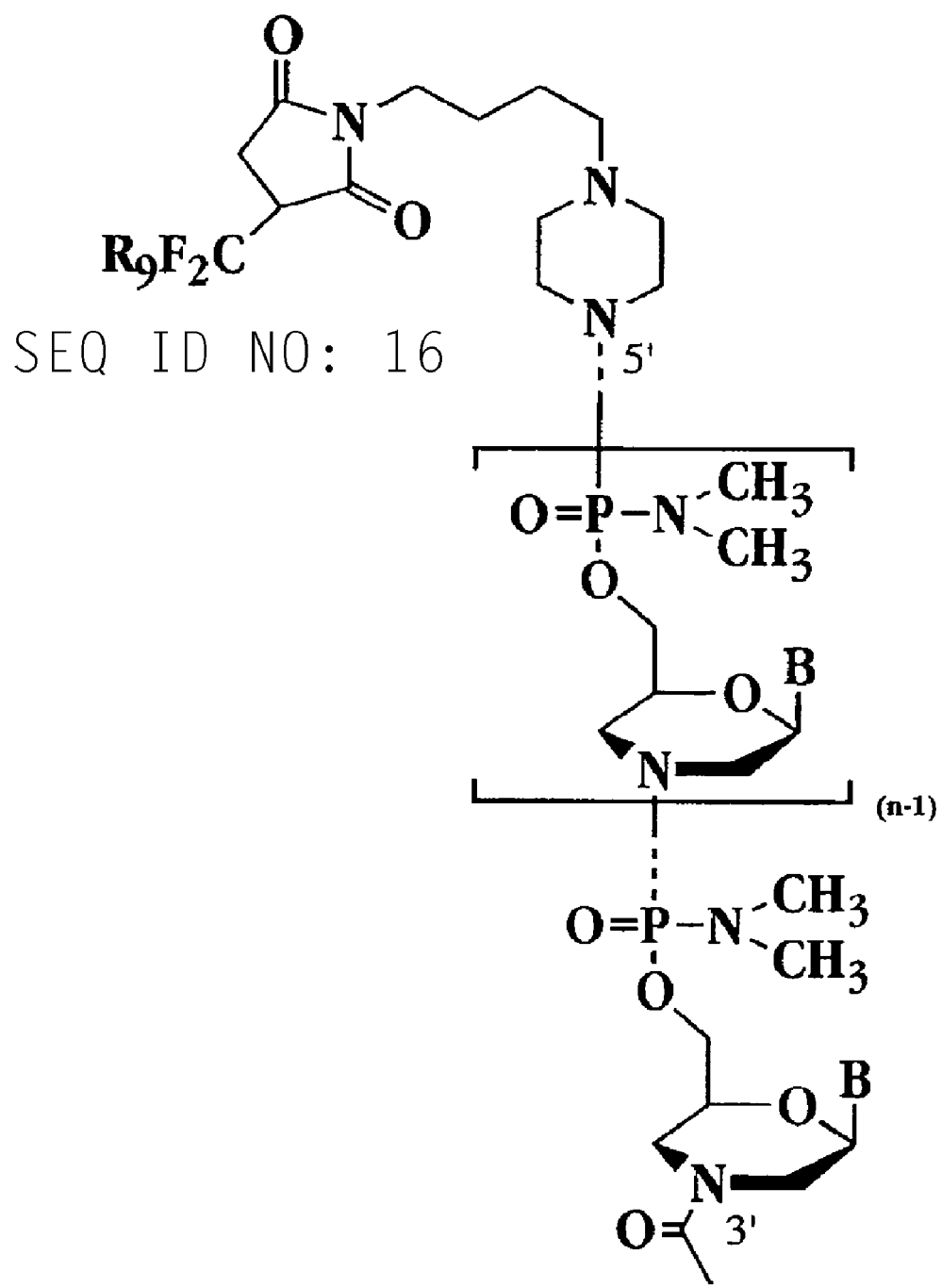
FIGS. 4A-D show oligomer-peptide conjugates and methods of their preparation, where
Figure 4B:
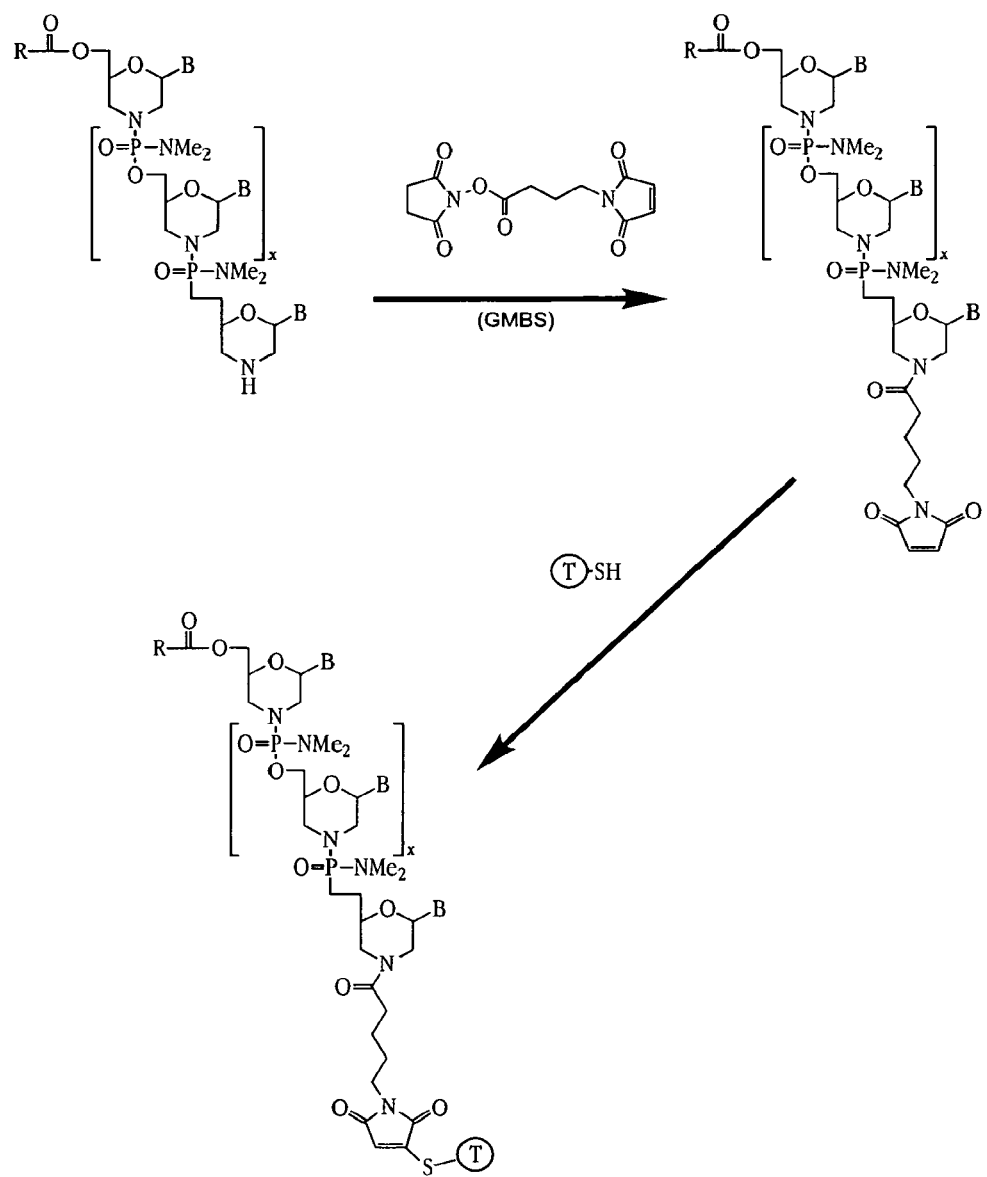

When the compound is a PMO, the transporter can be attached at the 5' end of the PMO, e.g. via the 5'-hydroxyl group, or via an amine capping moiety, as described in Example 3 and illustrated in FIG. 4A. Alternatively, the transporter may be attached at the 3' end, e.g. via a morpholino ring nitrogen, as shown in FIG. 4B, or via the side chain of an intersubunit linkage, either at a terminus or an internal linkage. The linker may also comprise a direct bond between the carboxy terminus of a transporter peptide and an amine or hydroxy group of the PMO, formed by condensation promoted by e.g. carbodiimide.

Linkers can be selected from those which are non-cleavable under normal conditions of use, e.g., containing a thioether or carbamate bond. In some embodiments, it may be desirable to include a linkage between the transporter moiety and compound which is cleavable in vivo. Bonds which are cleavable in vivo are known in the art and include, for example, carboxylic acid esters, which are hydrolyzed enzymatically, and disulfides, which are cleaved in the presence of glutathione. It may also be feasible to cleave a photolytically cleavable linkage, such as an ortho-nitrophenyl ether, in vivo by application of radiation of the appropriate wavelength.

Figure 4C:
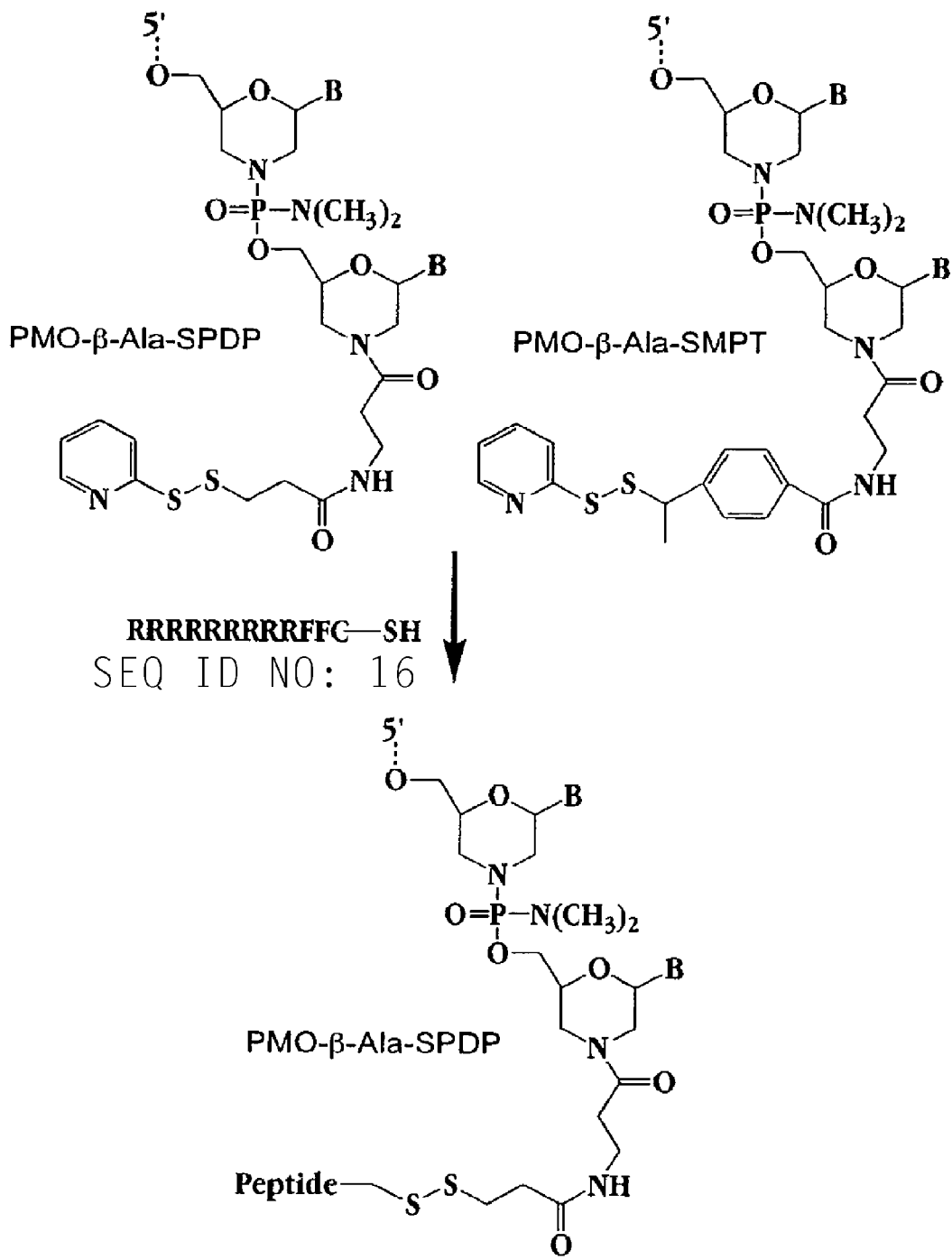
Figure 4D:
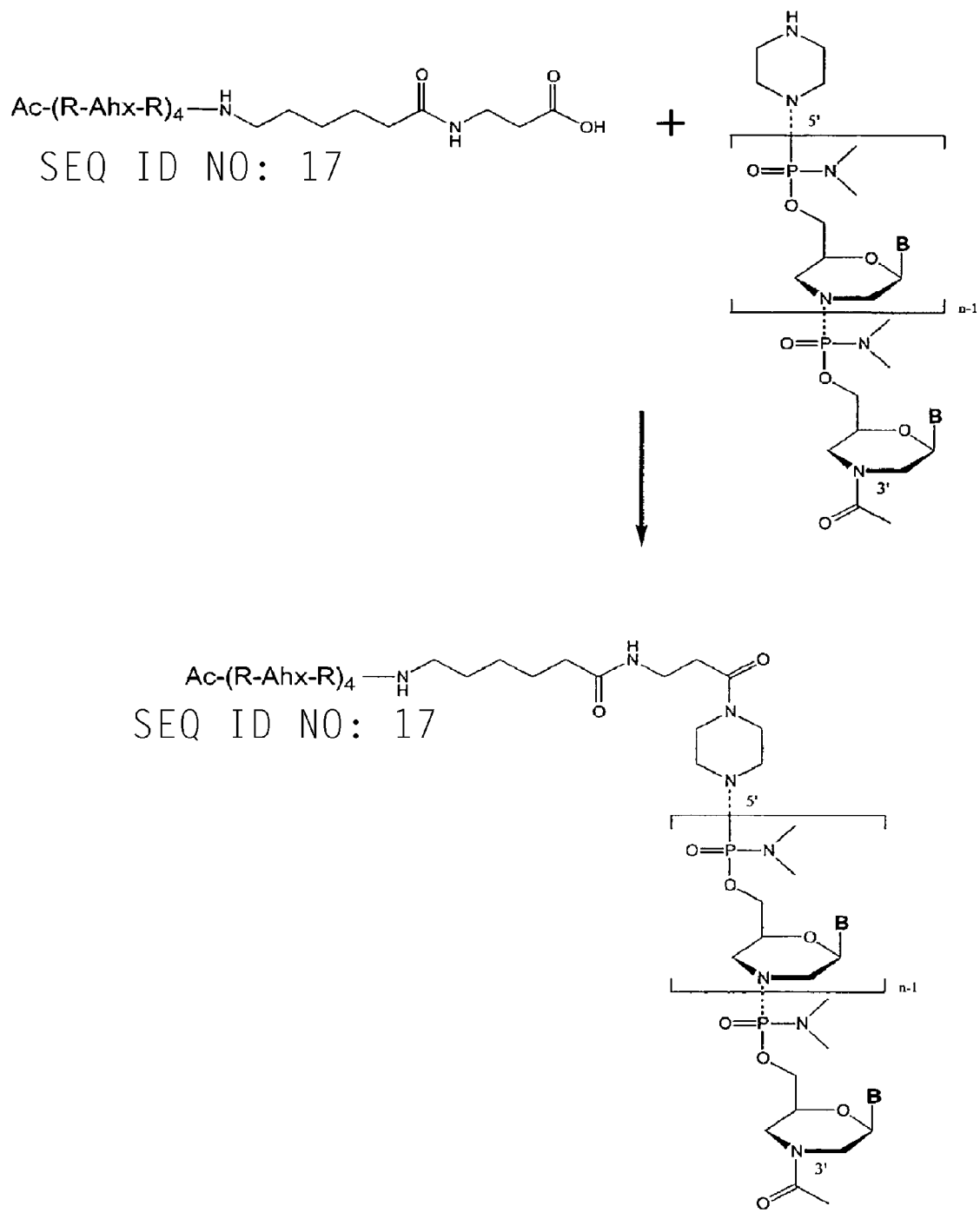

For example, the preparation of a conjugate having a disulfide linker, using the reagent N-succinimidyl 3-(2-pyridyldithio) propionate (SPDP) or succinimidyloxycarbonyl α-methyl-α-(2-pyridyldithio)toluene (SMPT), is illustrated in FIG. 4C. Exemplary heterobifunctional linking agents which further contain a cleavable disulfide group include N-hydroxysuccinimidyl 3-[(4-azidophenyl)dithio]propionate and others described in (Vanin and Ji 1981).

A Table of sequences of PMOs, peptide-conjugated PMOs and exemplary transporter peptides discussed in the following sections is provided below as Table 1. In general, the peptides include an N-terminal amino group and C-terminal amine (e.g., $NH_2$—RRRRRRRRRFFC—$CONH_2$ SEQ ID NO:16). Inosine substituted guanine residues are shown in bold.

TABLE 1

Exemplary PMOs, Peptide-conjugated PMOs and Transport Peptides

| PMOs | Sequence (5' to 3') | SEQ ID NO: |
|---|---|---|
| c-myc (AVI-4126) | ACG TTG AGG GGC ATC GTC GC | 1 |
| c-myc 398 | ACG TTG AGI GGC ATC GTC GC | 2 |
| c-myc 400 | ACG TTG AGG IGC ATC GTC GC | 3 |
| c-myc 402 | ACG TTG AIG IGC ATC GTC GC | 4 |
| c-myc 404 | ACG TTG AIG GIC ATC GTC GC | 5 |
| c-myc 406 | ACG TTG AGI IGC ATC GTC GC | 6 |
| c-myc 408 | ACG TTG AGI GIC ATC GTC GC | 7 |
| c-myc 410 | ACG TTG AII IGC ATC GTC GC | 8 |
| c-myc 412 | ACG TTG AGI IIC ATC GTC GC | 9 |
| c-myc 414 | ACG TTG AII IIC ATC GTC GC | 10 |

| Peptide-PMC | Sequence (amino to carboxy to 5' to 3') | |
|---|---|---|
| c-myc 36-01 | (RAhxR)$_4$Ahx-βAla-ACGTTGAGIGCATCGTCGC-3' | 11 |
| c-myc 36-02 (AVI-5126) | (RAhxR)$_4$Ahx-βAla-ACGTTGAIIGCATCGTCGC-3' | 12 |
| c-myc 36-03 | (RAhxR)$_4$Ahx-βAla-ACGTTGAGIIICATCGTCGC-3' | 13 |
| (RAhxR)$_4$-c-myc | (RAhxR)$_4$Ahx-βAla-ACGTTGAGGGGCATCGTCGC-3' | 14 |
| R$_9$F$_2$Ahx-c-myc | RRRRRRRRRFF-Ahx-ACGTTGAGGGGCATCGTCGC | 15 |

| Peptides | Sequence (amino to carboxy) | |
|---|---|---|
| R$_9$F$_2$C | RRRRRRRRRFFC | 16 |

TABLE 1-continued

Exemplary PMOs, Peptide-conjugated
PMOs and Transport Peptides

| | | SEQ ID NO: |
|---|---|---|
| (RAhxR)$_4$ | RAhxRRAhxRRAhxRRAhxR | 17 |
| (RAhx)$_8$ | RAhxRAhxRAhxRAhxRAhxRAhxRAhxRAhx | 18 |

C. Inosine-Substitution in the Oligomer Compound

In studies conducted in support of the present invention, and reported below, it was observed that coupling an arginine-rich peptide to an oligomer compound having a string of four or more guanine bases (that is, targeted against a sequence having a run of four or more cytosine bases), with the objective of enhancing the cellular uptake of the compound, created two critical problems, both unexpected. First, the presence of the arginine-rich polypeptide caused aggregation of the conjugate during the process of purification on a cationic ion exchange resin. Secondly, the antisense activity of the compound against the target was significantly reduced.

As described in Examples 2 and 3, aggregation of the conjugate is a major hurdle to overcome in the synthesis of arginine-rich peptides conjugated to G-rich PMOs such as the c-myc PMO (AVI-4126, SEQ ID NO:1). Initial preparations of peptide conjugated c-myc PMO produced discrepancies in the subsequent analysis. The mass spectrum of the conjugate was as expected but the analytical strong cation exchange (SCX) HPLC gave several different peaks with quite different retention times. The multiple peaks corresponded to different aggregate forms of the conjugate. The results described in Examples 4 and 5 demonstrate that guanine-rich PMO sequences are involved in the aggregation observed in the strong cation exchange (SCX) HPLC of the c-myc PMO, and that substitution of inosine bases for one or more of the contiguous guanine bases reduced or eliminated this aggregation. As listed in Table 1, one exemplary structure for AVI-5126 (SEQ ID NO:12) contains three inosine residues and forms no aggregated species even under conditions that strongly favor aggregation.

The aggregation phenomenon observed when arginine-rich transport peptides are conjugated to PMOs is not limited to this class of nucleic acid analogs. Other uncharged nucleic acids or nucleic acid analogs, including other morpholino backbones, methylphosphonates, phosphorothioates and phosphodiesters (i.e., DNA and RNA) and PNAs all have the same potential for aggregation when conjugated to an arginine-rich polypeptide, and thus the potential for improvement by the inosine-to-guanine base substitution of the invention.

D. Improved Steric Blocking Properties of Inosine-Substituted, Arginine-Rich Peptides Inosine substituted PMOs that target the c-myc gene were tested in a cell free rabbit reticulocyte lysate (RRL) assay described in Example 4. As described in this example and shown in FIG. 6 increasing numbers of inosine for guanine substitutions correlated with a decreased inhibition of translation. The PMO with four inosine for guanine substitutions (SEQ ID NO:10) was the least effective at inhibiting translation whereas the PMOs with only one I for G substitution (SEQ ID NOS:2 and 3) were the most effective of all the inosine containing PMOs. The control c-myc PMO with no inosine substitutions (SEQ ID NO:1) had the highest level of inhibition in this assay. The decreased inhibition of translation observed with inosine containing PMOs is consistent with the loss of one hydrogen bond between I:C base pairs as compared to G:C base pairs with three hydrogen bonds. The lower Tm between the targeting PMO and its target may play a role in the relative loss of steric blocking that the RRL assay measures.

Figure 6:
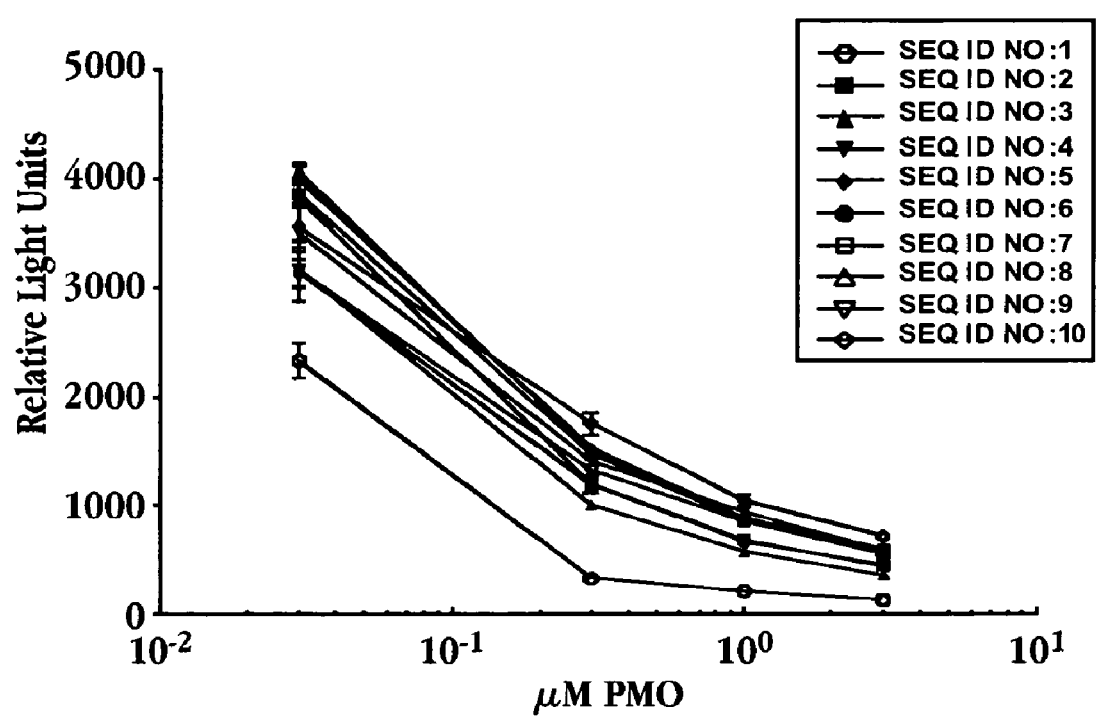
FIG. 6 shows graphically the results of cell-free rabbit reticulocyte lysate translation inhibition using various unconjugated inosine substituted and nonsubstituted c-myc oligomers.
Figure 7:
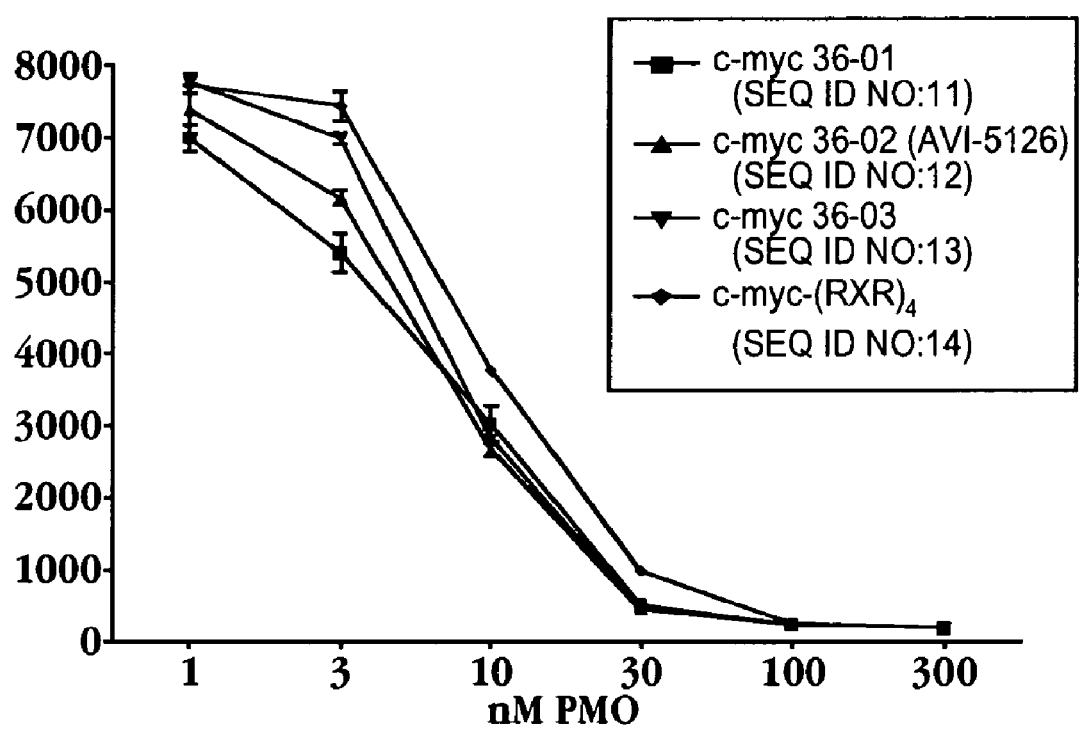
FIG. 7 represents the inhibition of cell-free translation using arginine-rich peptide conjugated c-myc PMOs with or without inosine substitutions.

Three of the c-myc PMOs with inosine for guanine substitutions described above were conjugated to the (RAhxR)$_4$ delivery peptide and tested for their ability to inhibit cell free translation using the same pCNmycluc plasmid and RRL system described in Example 4. As shown in FIG. 7 and described in Example 5, the least inhibitory PMO was observed to be the control peptide conjugated c-myc PMO sequence with no inosine substitutions (SEQ ID NO:14). In contrast, the compounds with inosine substitutions demonstrated significantly greater inhibition of translation. Shown in FIG. 7 are (RahxR)$_4$ peptide PMO conjugates with either two or three inosine substitutions (SEQ ID NOS:11-13). The improved translational inhibition of the peptide-conjugated, inosine-substituted PMO is in marked contrast to the decreased inhibition observed with the unconjugated PMOs described in Example 4 and shown in FIG. 6.

The enhanced steric blocking inhibition that arginine-rich peptides confer to antisense PMO completely overcomes the decreased steric blocking properties observed with unconjugated inosine substituted PMO. Based on the results described in Example 5 and shown in FIG. 7, PMO with inosine substitutions have significantly enhanced steric blocking properties relative to non-inosine substituted PMO.

III. Applications

The conjugates of the present invention are useful in treatment of vascular proliferative disorders such as restenosis. Areas of vessel injury include, for example, restenosis or renarrowing of the vascular lumen following vascular intervention, such as coronary artery balloon angioplasty, with or without stent insertion. Restenosis is believed to occur in about 30% to 60% of lesions treated by angioplasty and about 20% of lesions treated with stents within 3 to 6 months following the procedure. (See, e.g., Devi, N. B. et al., *Cathet Cardiovasc Diagn* 45(3):337-45, 1998). Stenosis can also occur after a coronary artery bypass operation, wherein heart surgery is done to reroute, or "bypass," blood around clogged arteries and improve the supply of blood and oxygen to the heart. In such cases, the stenosis may occur in the transplanted blood vessel segments, and particularly at the junction of replaced vessels. Stenosis can also occur at anastomotic junctions created for dialysis.

In this aspect, a PMO conjugate, preferably targeting c-myc, is employed in a coated stent, or by an ex vivo soaking solution for treatment of saphenous veins, or otherwise delivered to the site of vascular injury. Microbubble compositions have been found particularly useful in delivery of attached molecules, such as oligonucleotides, to areas of thrombosis or vessel injury, e.g. damaged endothelium (see e.g. PCT Pubn.

No. WO 2000/02588) as well as to selected organs such as the liver and kidney. A preferred antirestenotic composition is an inosine-substituted, anti-c-myc PMO conjugated to an (RAhxR)$_4$ transport peptide through an Ahx-βAla linker (e.g., SEQ ID NO:12).

The PMO conjugates targeting the c-myc gene described herein are also useful in the treatment of cancer in general and bladder cancer in particular. Transurethral administration of a PMO conjugate, preferably targeting c-myc, in conjunction with chemotherapy provides enhanced anticancer activity as described (Knapp, Mata et al. 2003) and as described in co-owned and co-pending U.S. application Ser. No. 10/151,008 which is incorporated herein by reference in its entirety. A preferred anticancer composition is an inosine-substituted, anti-c-myc PMO conjugated to an (RAhxR)$_4$ transport peptide through an Ahx-βAla linker (e.g., SEQ ID NO:12).

The following examples illustrate various embodiments of the invention, without limitation.

Example 1

Peptide Synthesis and Conjugation to PMO

Peptides were synthesized by Fmoc Solid Phase Peptide Synthesis, referred to herein as SPPS. A p-benzyloxybenzyl alcohol resin was used for synthesis of peptides with a C-terminal acid, while a Rink Amide MBHA resin was used for peptide amides. Both resins are available from Novabiochem (San Diego, Calif.). A typical synthesis cycle began with N-terminal deprotection via 20% piperidine. Then, N-α-Fmoc-protected amino acids were coupled to the growing peptide chain by activation with 2-(1H-Benzotriazole-1-yl)-1,1,3,3-tetramethyluronium hexafluorophosphate (HBTU) in the presence of N,N-diisopropylethylamine (DIEA). Arginine side chains were protected with the 2,2,4,6,7-pentamethyldihydrobenzofuran-5-sulfonyl (Pbf) protecting group, cysteine with trityl, and lysine side chains with t-butoxycarbonyl (Boc). The cycle was repeated until all of the amino acids were added, in a carboxy-to-amino direction, in the desired sequence. Cleavage from the synthesis resin and side chain deprotection were carried out simultaneously by treating the peptidyl-resin with a solution of 2.5% H2O, 2.5% triisopropyl silane (TIS), and 95% trifluoroacetic acid (TFA). For peptides containing a cysteine residue, 2.5% 1,2-ethanedithiol (EDT) was added to the cleavage cocktail. Crude peptides were isolated by precipitation using a tenfold excess of diethyl ether. Strong cation exchange HPLC utilizing Source 15S resin (Amersham Biosciences, Piscataway, N.J.) was used for purification, followed by a reversed phase desalt employing Amberchrom 300M resin (Tosoh Bioscience, Montgomeryville, Pa.). Desalted peptides were lyophilized and analyzed for identity and purity by matrix assisted laser desorption ionization time of flight mass spectroscopy (MALDI-TOF MS), strong cation exchange high performance liquid chromatograph (SCX HPLC), and capillary electrophoresis (CE).

Peptides containing various C-terminal hydrophobic linkages were prepared as follows. Peptides were prepared for direct condensation with an amine or hydroxy group of the PMO by including combinations of natural and/or non-natural amino acids at the C-terminal end of the peptide during SPPS. Specifically, the linkages were comprised of the amino acids glycine, beta-alanine, and/or 6-aminohexanoic acid, used in different combinations of one or two residues. Peptide synthesis was otherwise identical to the synthesis of other peptide acids.

Peptides with masked amine groups for direct condensation with an amine or hydroxy group of a PMO were prepared as follows. Free peptide amino groups interfere with direct condensation of the carboxy terminus of the peptide with an amine or hydroxy group of a PMO, and must therefore be masked. Peptide sequences, such as rTat and pTat (Table 1), that contain amine side-chains were prepared by using the 1-(4,4-dimethyl-2,6-dioxocyclohex-1-ylidene)ethyl (Dde) amine side chain protecting group. Peptide synthesis was otherwise identical to the synthesis of other peptide acids. Lysine Dde groups survived the resin cleavage and deprotection of other amino acid side chain protecting groups. The side chain amines remain masked by Dde through conjugation and are subsequently deprotected by treatment with 2% hydrazine in DMF.

Attachment of a transport peptide at the 5' termini of the PMO was performed via an amide bond as follows. A C-terminally reactive peptide-benzotriazolyl ester was prepared by dissolving the peptide-acid (15 µmol), HBTU (14.25 µmol), and HOBt (15 µmol) in 200 µl NMP and adding DIEA (22.5 µmol). Immediately after addition of DIEA, the peptide solution was added to 1 ml of a 12 mM solution of 5'-piperazine-functionalized, 3'-acetyl-PMO in DMSO. After 180 minutes at 30° C., the reaction was diluted with a four-fold excess of water. The crude conjugate was purified first through a CM-Sepharose weak cation exchange column (Sigma, St. Louis, Mo.) to remove unconjugated PMO, and then through a reversed phase column (HLB column, Waters, Milford, Mass.). The conjugate was lyophilized and analyzed by MALDI-TOF MS, SCX HPLC, and CE.

Example 2

G-Rich Oligomers Form G-Tetraplex Aggregates when Conjugated to Arginine-Rich Peptides This example details the development of an arginine-rich peptide-PMO conjugate that targets the c-myc gene for a coronary artery bypass graft (CABG) clinical application. The goal of the project described in this example was to develop processes for the synthesis and purification of the conjugate with acceptable yield and purity. Furthermore, methods for analysis of the conjugate must characterize it and identify impurities throughout the synthetic process and in any formulations used in the clinic. Quantitation of the amount of free peptide remaining in the product is probably the most critical analytical capability as free peptide is potentially more toxic than conjugate or free PMO.

As will be shown below, it is clear that aggregation through the formation of intramolecular G-quartets is a major hurdle to overcome in the synthesis of arginine-rich peptides conjugated to G-rich PMOs such as the c-myc PMO (AVI-4126, SEQ ID NO:1). In light of this, several problems require resolution prior to the further development of this compound. First, is it possible to produce a non-aggregated form of the conjugate? Second, is it possible to develop an analytical method that is neither aggregating nor disaggregating that will give us an accurate assessment of the form of a given sample? Finally, what aggregate form, if any, will the conjugate assume when formulated in an injection buffer such as PBS?

Initial preparations of peptide conjugated cmyc PMO produced glaring discrepancies in the subsequent analysis. The mass spectrum was as expected but the analytical strong cation exchange (SCX) HPLC gave several different peaks with quite different retention times. The multiple peaks corresponded to different aggregate forms of the conjugate.

The evidence for aggregation comes from the first attempt at purifying it by preparative SCX HPLC. 118 OD$_{260}$ of R$_9$F$_2$Ahx-cmyc (SEQ ID NO:15) was loaded on a 20 ml Source 15S HPLC column and run in a KH$_2$PO$_4$ buffer at pH 4.75, with elution via 1.5M KCl. Both A and B buffers contained 25% acetonitrile (ACN). The conjugate eluted from the column as one major peak, eluting just after the free peptide but subsequent fraction analysis revealed that later eluting peaks had been enriched. The later-eluting peaks correspond to multimeric aggregate forms of the conjugate. Evidence that the later eluting peaks are multimeric aggregate forms of the conjugate, with their longer retention times due to their increased charge, was provided by the observation that the salty conditions of the SCX purification favor the aggregate forms, while low salt conditions favor the free form. Salt is known to enhance the formation of quadruplex GROs via G-quartets. Loading a conjugate on a SCX HPLC column in 1.5M KCl enriched the second of the two later-eluting peaks, and decreased the amount of the early nonaggregated peak. Loading in either 2M guanidinium chloride or 6M urea greatly reduced the amount of later-eluting peaks, and left the early-eluting peak unaffected. The aggregation state of the molecule can therefore be manipulated by changing the loading environment. This provided additional evidence that the later-eluting peaks correspond to aggregate forms of the conjugate, the traditional disaggregants urea and guanidinium are apparently effective in disaggregating the conjugate as it is loaded onto the resin.

The effect of heat on the analytical SCX HPLC provided additional evidence for aggregation. This chromatography was performed using a Source 15S tricorn SCX column placed inside a column oven. When metal cations are excluded from the chromatography altogether, and replaced with guanidinium, the application of heat to the column makes the later-eluting peaks disappear. The percentage of aggregated conjugate decreases as the temperature of the column is increased from room temperature up to 65° C. The "melting-out" phenomenon is not observed when sodium is used as the cation throughout the chromatography, suggesting that metal cations stabilize the aggregated species. This makes sense when viewed in the context of the aforementioned SCX purification attempt, where potassium was ubiquitous and the aggregate form predominated.

The fact that the conjugate's aggregate form has a much longer retention time suggested that, however the molecules are interacting, the charges on the arginine side-chains are still available for interaction with the ion-exchange resin. This would be the case if the PMO-portions of conjugate molecules were interacting with each other to form multimeric aggregates where the peptide portions weren't involved in the interaction.

The aggregation problem seems to be unique to the c-myc PMO sequence, or at least to guranine-rich oligomers (GROs). The conjugation of similar peptides to sequences that have low G-content present no aggregation problems. Conjugates of other PMOs with consecutive G-runs, exhibit the same type of aggregation on SCX HPLC. The linker between the PMO and the peptide doesn't seem to have any affect on aggregation. The N-(4-maleimidobutyryloxy) succinimide ester (GMBS) thioether linkage gives a very similar SCX elution pattern to Gly2-Ahx, Ahx2, or Ahx amide linkages. Finally, a more recent peptide used in our c-myc conjugates, (RAhxR)$_4$—, even though it is 58% longer than the previous R$_9$F$_2$—, gives the same aggregate SCX elution pattern as the shorter peptide. Therefore, aggregation occurs with any arginine-rich peptide, and with all of the linkages employed to date. Since no aggregation is observed when the same peptides with their various linkages are conjugated to "low-G" PMO sequences, we attribute the phenomenon to the G-rich nature of the c-myc PMO sequence.

The observed aggregation observed with conjugated GRO is consistent with PMO to PMO interactions that form the G-tetraplex structures seen in DNA and RNA with runs of consecutive guanines. The PMO sequence of the cmyc 20-mer PMO described above (SEQ ID NO:1) is 5'-ACG TTG AGG GGC ATC GTC GC-3' it's four-G run spanning positions 8-11. Evidence for the formation of G-tetraplex structures is provided when the effects of different cations on the degree of aggregation is measured by SCX HPLC. It is well-known that cationic interactions are important for coordinating DNA and RNA tetraplexes.

Example 3

Figure 5:
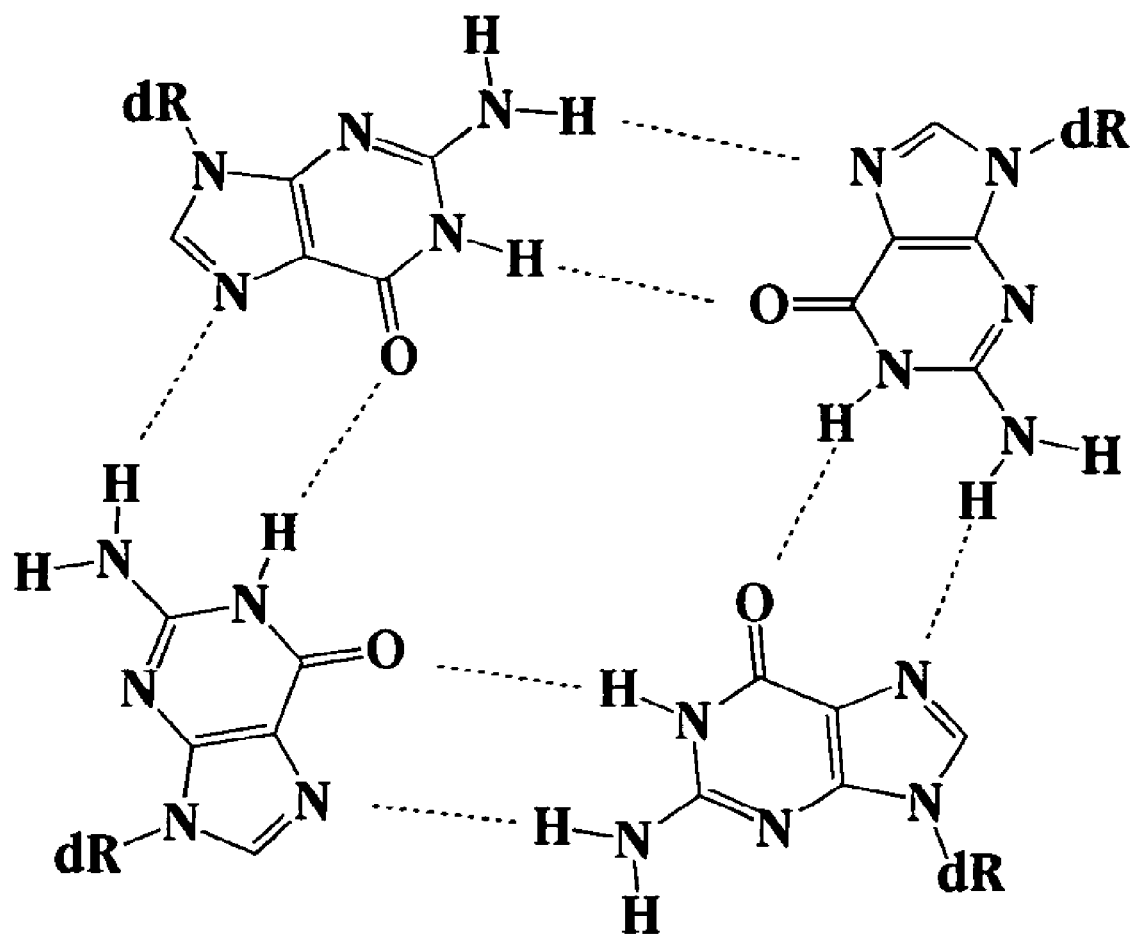
FIG. 5 is a schematic representation of G-quartet base pairs where PMO represents either the intermolecular or intramolecular morpholine residue of the oligomer backbone.

Inosine Substituted for Guanine Prevents Aggregation of G-Rich Oligomers Conjugated to Arginine-Rich Peptides It has long been recognized that guanine-rich nucleic acid sequences can adopt intermolecular or intramolecular quadruplex structures that are stabilized by the presence of G-quartets (see FIG. 5). G-quartets are stacked planar hydrogen-bonded guanine tetramers and cause guanine-rich nucleic acids to form quadruplex structures. The potential roles of quadruplex formation in vivo have been investigated because some biologically important G-rich sequences are capable of forming G-quartets under physiological conditions in vitro. In addition, the number of reports describing specific G-quartet-binding proteins is now considerable (Shafer and Smirnov 2000).

G-rich oligomers (GROs) can form a variety of possible quadruplex structures, depending on both thermodynamic and kinetic considerations. The structures formed can be influenced by oligonucleotide base sequence and concentration, as well as the conditions (temperature and buffer) used for annealing, especially the presence of monovalent cations such as K$^+$ and Na$^+$. Quadruplexes can be formed by one, two or four molecules of oligonucleotide, which are referred to as monomer, dimer and tetramer structures, respectively. Monomer and dimer quadruplexes have been classified further based on the positioning of their loop regions into chair (lateral loop) or basket (diagonal loop) forms. The relative strand orientation (5' to 3' polarity) of the four strands of the quadruplex may be parallel, antiparallel, or mixed (Dapic, Abdomerovic et al. 2003).

In order to disrupt hydrogen-bonding interactions that facilitate G-tetraplex structures, nine PMOs were synthesized with inosine substituted for guanine in different positions within the four-G run of the c-myc PMO (SEQ ID NO:1). The inosine containing PMOs are listed in Table 1 as SEQ ID NOS: 2-10. After conjugation with peptide, analysis was performed under highly aggregating SCX HPLC conditions. Since the conditions are maximally aggregating, they should be a rigorous test of each molecule's relative tendency to aggregate.

Ac-(Arg-Ahx-Arg)$_4$-Ahx-βAla-OH peptide, as the trifluoroacetate salt, was conjugated to the unmodified and nine inosine-modified cmyc PMO 20-mer sequences listed Table 1 (SEQ ID NOS:1-10). Conjugations were carried out in the usual manner, using HBTU coupling in NMP/DMSO. The reactions proceeded with stirring at 35° C. for 180 minutes. The reaction mixtures were diluted with 3 ml H$_2$O, loaded onto 2 ml CM-sepharose columns, washed with 2 ml ACN and 1 ml H$_2$O. Conjugates were eluted with 4 ml of 2M guanidinium chloride. The salty conjugate solutions eluted from the ion-exchange columns were desalted by loading on 2 ml Waters HLB reversed-phase columns, washing with 4 ml $H_2O$, and eluting with 4 ml 50% ACN. Finally, the solutions were lyophilized.

Analysis of the conjugate by MALDI-TOF MS suggested a clean product, the major impurities due to N-1 truncated PMO sequences. HPLC was performed using a Bio-Rad Bio-Logic HR HPLC system. The column used for all runs was a Tricorn Source 15S 4.6/100 PE (Amersham Biosciences; product 17-5182-01). The buffer system used was 10 mM $Na_2HPO_4$ in 25% ACN at pH 7.5, with elution via 1.5M NaCl. Samples were all loaded in buffer A. A flow rate of 1 ml/min. with a 20-75% B/14 column volume gradient was employed for all runs. Chromatographic results are given in Table 2 below as integrated peak values. It should be noted that a small peak representing a chemical impurity and approximately 7% of the integration total was present in all the chromatograms.

The substitution of inosine for guanine had an obvious effect on the relative amount of aggregation. With the substitution of just one guanine, in position 9 or 10, the percent conjugate in the aggregate form dropped from 79% to an average of 56%. Three of the sequences with two substitutions, (I8, I10), (I8, I11), and (I9, I11), had chromatograms with an average 20% aggregated conjugate. Substituting the two central guanines of the four-G run had a greater effect, giving only 2.7% aggregate. When three or more of the guanines (I9, I10) were substituted, aggregation was totally eliminated.

TABLE 2

Aggregation of Inosine-substituted PMO-peptide Conjugates

| Sequence Name | SEQ ID NO | # Inosine Residues | | % Unaggregated |
|---|---|---|---|---|
| (RAhxR)₄AhxβAla-cmyc(I10) | 19 | 1 | 36.04 | 56.66 |
| (RAhxR)₄AhxβAla-cmyc(I8, I10) | 20 | 2 | 68.73 | 21.91 |
| (RAhxR)₄AhxβAla-cmyc(I8, I11) | 21 | 2 | 66.06 | 23.68 |
| (RAhxR)₄AhxβAla-cmyc(I9, I10) | 22 | 2 | 88.39 | 2.67 |
| (RAhxR)₄AhxβAla-cmyc(I9, I11) | 23 | 2 | 75.46 | 16.21 |
| (RAhxR)₄AhxβAla-cmyc(I8, I9, I10) | 24 | 3 | 91.74 | 0.0 |
| (RAhxR)₄AhxβAla-cmyc(I9.I10, I11) | 25 | 3 | 92.26 | 0.0 |
| (RAhxR)₄AhxβAla-cmyc(I8, I9, I10, I11) | 26 | 4 | 91.92 | 0.99 |
| (RAhxR)₄AhxβAla-cmyc | 27 | 0 | 7.72 | 78.93 |
| (RAhxR)₄AhxβAla-cmyc(I9) | 28 | 1 | 37.86 | 55.06 |

Example 4

Inhibition of Cell Free Translation Using PMO with Inosine for Guanine Substitutions The coding sequence for firefly luciferase (fLUC) was subcloned into the multiple cloning site of plasmid pCi-Neo (Promega) at the Sal I and Not I sites and the resulting plasmid named pCNlucr. A 30 base pair region surrounding the ATG start codon of the human c-myc gene (5'-AGCCTCCCGC-GACGATGCCCCTCAACGTTA-3' (SEQ ID NO:29), Genbank accession number V00568) was subcloned into the Nhe I and Sal I sites of pCNlucr and named pCNmycluc. This placed the c-myc coding sequences in frame with the amino acid coding sequences of the fLUC gene (c-myc:fLUC). A PMO targeting this region of c-myc, AVI-4126, is listed as SEQ ID NO:1. Inosine-substituted PMOs with various numbers and positions of guanine residues replaced with inosine and that target the c-myc start codon region are listed as SEQ ID NOS:2-10.

All the plasmids described above have the T7 RNA polymerase promoter upstream of the c-myc:fLUC sequences and allowed RNA to be produced from the plasmid, after linearization with NotI, using the T7 polymerase-based Megascript kit and protocol (Ambion). In vitro translations were carried out using transcribed RNA at a final concentration in each reaction of 1 nM, with 12 μl nuclease-treated rabbit reticulocyte lysate (Promega) in addition to PMO, (RAhxR)₄-PMO, or water. 10 μl of translation reaction was mixed with 50 μl luciferase assay reagent (Promega) according to manufacturer's instructions and light emission was read on a FLx800 microplate luminometer (BIO-TEC Instruments). Reactions were assayed for relative light units with the KC Junior program (BIO-TEC) using the luminescence function and a sensitivity setting of 125. Twelve reactions were assayed at one time, including water-control reactions in the first and last well of each row. The relative light units (RLU) produced by each reaction (n=3) as a function of PMO or (RAhxR)₄-PMO concentration was expressed as shown in FIGS. 6 and 7.

Various inosine substituted PMOs that target the c-myc gene were tested in the cell free rabbit reticulocyte lysate (RRL) assay described above. As shown in FIG. 6, increasing numbers of inosine for guanine substitutions correlated with a decreased inhibition of translation. The PMO with four inosine for guanine substitutions (SEQ ID NO:10) was the least effective at inhibiting translation. The PMOs with only one I for G substitution (SEQ ID NOS:2 and 3) were the most effective of all the inosine containing PMOs. The most effective PMO was the control c-myc PMO with no inosine substitutions (SEQ ID NO:1). The decreased inhibition of translation observed with inosine containing PMOs is proposed to be due to the loss of one hydrogen bond between I:C base pairs as compared to G:C base pairs with three hydrogen bonds.

Example 5

Enhanced Inhibition of Cell Free Translation with Inosine Substituted Peptide-PMO Conjugates Three different c-myc PMOs with various inosine for guanine substitutions were conjugated to the (RahxR)₄ delivery peptide and tested for their ability to inhibit cell free translation using the same pCNmycluc plasmid and RRL system described in Example 4. As shown in FIG. 7, the least inhibitory PMO was observed to be the control peptide conjugated c-myc PMO sequence with no inosine substitutions (SEQ ID NO:14). The compounds with inosine substitutions demonstrated significantly greater inhibition of translation. Shown in FIG. 7 are RahxR peptide PMO conjugates with either two or three inosine substitutions (SEQ ID NOS:11-13). The improved translational inhibition of the peptide conjugated, inosine substituted PMO is in marked contrast to the decreased inhibition observed with the unconjugated PMOs described in Example 3 and shown in FIG. 6. The enhanced steric blocking inhibition that arginine-rich peptides confer to antisense PMO completely overcomes the decreased steric blocking properties observed with unconjugated inosine substituted PMO. Based on the results shown in FIG. 7, PMO with inosine substitutions are unexpectedly enhanced to a greater degree than non-inosine substituted PMO. The mechanism for the enhanced steric blocking properties that arginine-rich peptides confer to inosine substituted PMO is currently unknown. However, the utility both in the synthesis and therapeutic potential of these improved antisense PMO is considerable.

Sequence Listing

| PMOs | Sequence (5' to 3') | SEQ ID NO: |
|---|---|---|
| c-myc (AVI-4126) | ACG TTG AGG GGC ATC GTC GC | 1 |
| c-myc 398 | ACG TTG AGI GGC ATC GTC GC | 2 |
| c-myc 400 | ACG TTG AGG IGC ATC GTC GC | 3 |
| c-myc 402 | ACG TTG AIG IGC ATC GTC GC | 4 |
| c-myc 404 | ACG TTG AIG GIC ATC GTC GC | 5 |
| c-myc 406 | ACG TTG AGI IGC ATC GTC GC | 6 |
| c-myc 408 | ACG TTG AGI GIC ATC GTC GC | 7 |
| c-myc 410 | ACG TTG AII IGC ATC GTC GC | 8 |
| c-myc 412 | ACG TTG AGI IIC ATC GTC GC | 9 |
| c-myc 414 | ACG TTG AII IIC ATC GTC GC | 10 |
| Peptide-PMC | Sequence (amino to carboxy to 5' to 3') | |
| c-myc 36-01 | (RAhxR)$_4$Ahx-βAla-ACGTTGAGIIGCATCGTCGC-3' | 11 |
| c-myc 36-02 (AVI-5126) | (RAhxR)$_4$Ahx-βAla-ACGTTGAIIIGCATCGTCGC-3' | 12 |
| c-myc 36-03 | (RAhxR)$_4$Ahx-βAla-ACGTTGAGIIICATCGTCGC-3' | 13 |
| (RAhxR)$_4$-c-myc | (RAhxR)$_4$Ahx-βAla-ACGTTGAGGGGCATCGTCGC-3' | 14 |
| R$_9$F$_2$Ahx-c-myc | RRRRRRRRRFF-Ahx-ACGTTGAGGGGCATCGTCGC | 15 |
| Peptides | Sequence (amino to carboxy) | |
| R$_9$F$_2$C | RRRRRRRRRFFC | 16 |
| (RAhxR)$_4$ | RAhxRRAhxRRAhxRRAhxR | 17 |
| (RAhx)$_8$ | RAhxRAhxRAhxRAhxRAhxRAhxRAhxRAhx | 18 |

---

The invention claimed is:

1. A method for enhancing the cellular uptake of a substantially uncharged antisense oligonucleotide compound, wherein the compound comprises a base sequence complementary to a string of at least four contiguous cytosine bases, the base sequence comprising one or more inosine bases and no more than three contiguous guanine bases, the method comprising forming a conjugate of the compound and an arginine-rich peptide.

2. The method of claim 1, wherein the position of the one or more inosine bases in the base sequence limits the number of contiguous guanine bases in the base sequence to two or fewer.

3. The method of claim 1, wherein the base sequence comprises at least two inosine bases.

4. The method of claim 1, wherein the conjugate has enhanced water solubility during a purification step involving conjugate binding to and release from a cationic ion exchange resin, wherein the enhanced water solubility is relative to a second conjugate which is identical to the conjugate except that the second conjugate comprises four or more contiguous guanine bases.

5. The method of claim 1, wherein the compound targets a region that includes the start codon in an mRNA, and the conjugate comprises an enhanced ability to block translation of the protein encoded by the mRNA in a cell-free protein translation system, wherein the enhanced ability to block translation is relative to a second conjugate which is identical to the conjugate except that the second conjugate comprises four or more contiguous guanine bases.

6. The method of claim 1, wherein the arginine-rich peptide comprises 8 to 16 subunits including X subunits, Y subunits and optional Z subunits, wherein the arginine-rich peptide includes at least six X subunits, at least two Y subunits and at most three Z subunits, where >50% of the subunits are X subunits, and where:
  (a) each X subunit is independently arginine or an arginine analog, the analog having the structure: $R^1N=C(NH_2)R^2$, where $R^1$ is H or R; $R^2$ is R, $NH_2$, NHR or $NR_2$, R is lower alkyl or lower alkenyl and may further include oxygen or nitrogen and $R^1$ and $R^2$ may together form a ring, wherein the side chain is linked to the amino acid via $R^1$ or $R^2$;
  (b) each Y subunit is independently a neutral amino acid having the structure: $—C(O)—(CHR)_n—NH—$, where
    (i) n is 2 to 7 and each R is independently H or methyl, or
    (ii) n is 1 and R is substituted or unsubstituted alkyl, alkenyl, alkynyl, aryl or aralkyl, wherein the substituted alkyl, alkenyl or alkynyl includes at most one heteroatom for every four carbon atoms; and (c) each Z subunit is independently alanine, asparagine, cysteine, glutamine, glycine, histidine, lysine, methionine, serine or threonine.

7. The method of claim 6, wherein the arginine-rich peptide has the sequence identified as SEQ ID NO:17.

8. The method of claim 1, wherein the compound comprises a sequence of morpholino subunits, each morpholino subunit comprising a phosphorus-containing linkage connecting the morpholino nitrogen of one morpholino subunit to an exocyclic carbon at the morpholino 3-position of an adjacent morpholino subunit.

9. The method of claim 8, wherein each morpholino subunit comprises a phosphorodiamidate linkage, and each morpholino subunit has independently the following structure:

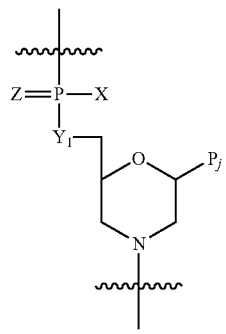

where $Y_1=0$, $Z=0$, Pj is a purine or pyrimidine base-pairing moiety capable of base-specific hydrogen bonding, to a base in a polynucleotide and X is alkyl, alkoxy, thioalkoxy or alkyl amino.

10. The method of claim 8, wherein the conjugate inhibits the synthesis of c-myc in a cellular system, and the compound has the sequence identified as SEQ ID NO: 1, where at least one of the four contiguous guanine (G) bases in the sequence is substituted with an inosine (I) base.

11. A method for preparing a conjugate of a substantially uncharged antisense oligonucleotide compound and an arginine-rich peptide, wherein the compound comprises a base sequence complementary to a string of at least four contiguous cytosine bases, the method comprising including at least one inosine bases in the base sequence such that the base sequence comprises no more than three contiguous guanine bases.

12. The method of claim 11, wherein including the at least one inosine base limits the number of contiguous guanine bases in the base sequence to two or fewer.

13. The method of claim 11, wherein at least two inosine bases are included.

14. The method of claim 11, wherein the compound targets a region that includes the start codon in an mRNA, and including the one or more inosine base enhances the ability of the conjugate to block translation of a protein encoded by the mRNA in a cell-free protein translation system, wherein the enhanced ability to block translation is relative to a second conjugate which is identical to the conjugate, except that the second conjugate comprises four or more contiguous guanine bases.

15. The method of claim 11, wherein the arginine-rich peptide comprises 8 to 16 subunits including X subunits, Y subunits, and optional Z subunits, wherein the arginine-rich peptide includes at least six X subunits, at least two Y subunits, and at most three Z subunits, where >50% of the subunits are X subunits, and where:

(a) each X subunit is independently arginine or an arginine analog, the analog having the structure: $R^1N=C(NH_2)R^2$, where $R^1$ is H or R; $R^2$ is R, $NH_2$, NHR, or $NR_2$, R is lower alkyl or lower alkenyl and may further include oxygen or nitrogen and $R^1$ and $R^2$ may together form a ring, wherein the side chain is linked to the amino acid via $R^1$ or $R^2$;

(b) each Y subunit is independently a neutral amino acid having the structure: —C(O)—(CHR)—NH—, where
(i) n is 2 to 7 and each R is independently H or methyl, or
(ii) n is 1 and R is substituted or unsubstituted alkyl, alkenyl, alkynyl, aryl or aralkyl, wherein the substituted alkyl, alkenyl or alkynyl includes at most one heteroatom for every four carbon atoms; and (c) each Z subunit is independently alanine, asparagine, cysteine, glutamine, glycine, histidine, lysine, methionine, serine or threonine.

16. The method of claim 15, wherein the arginine-rich peptide has the sequence identified as SEQ ID NO:17.

17. The method of claim 11, wherein the compound comprises a sequence of morpholino subunits, each morpholino subunit comprising a phosphorus-containing linkage connecting the morpholino nitrogen of one morpholino subunit to an exocyclic carbon at the morpholino 3-position of an adjacent morpholino subunit.

18. The method of claim 17, wherein each morpholino subunit comprises phosphorodiamidate linkages, and each morpholino subunit has independently the following structure:

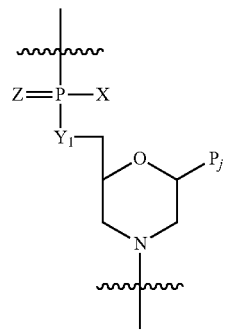

where $Y_1$ is O, Z is O, Pj is a purine or pyrimidine base-pairing moiety capable of base-specific hydrogen bonding, to a base in a polynucleotide; and X is alkyl, alkoxy, thioalkoxy or alkyl amino.

19. The method of claim 1, wherein the conjugate inhibits the synthesis of c-myc in a cellular system, and the compound has the sequence identified as SEQ ID NO: 1, where at least one of the four contiguous guanine (G) bases in SEQ ID NO: 1 is substituted with an inosine (I) base.

20. An oligomer-peptide conjugate comprising: (a) an arginine-rich peptide conjugated to a substantially uncharged antisense oligonucleotide compound, the compound comprising a base sequence complementary to a string of at least four contiguous cytosine bases and wherein the base sequence comprises at least one inosine bases and no more than three contiguous guanine bases.

21. The conjugate of claim 20, wherein the position of the at least one inosine bases in the base sequence limits the number of contiguous guanine bases in the base sequence to two or fewer.

22. The conjugate of claim 21, wherein the base sequence comprises at least two inosine bases.

23. The conjugate of claim 20, wherein the compound targets a region that includes the start codon in an mRNA, and the conjugate comprises an enhanced ability to block translation of a protein encoded by the mRNA in a cell-free protein translation system, wherein the enhanced ability to block translation is relative to a second conjugate which is identical to the conjugate, except that the second conjugate comprises four or more contiguous guanine bases.

24. The conjugate of claim 20, wherein the arginine-rich peptide comprises 8 to 16 subunits including X subunits, Y subunits, and optional Z subunits, wherein the arginine-rich peptide includes at least six X subunits, at least two Y subunits, and at most three Z subunits, where >50% of the subunits are X subunits, and where:
  (a) each X subunit is independently arginine or an arginine analog, the analog having the structure: $R^1N=C(NH_2)R^2$, where $R^1$ is H or R; $R^2$ is R, $NH_2$, NHR, or $NR_2$, R is lower alkyl or lower alkenyl and may further include oxygen or nitrogen and $R^1$ and $R^2$ may together form a ring, wherein the side chain is linked to the amino acid via $R^1$ or $R^2$;
  (b) each Y subunit is independently a neutral amino acid having the structure: —C(O)—(CHR)$_n$—NH—, where (i) n is 2 to 7 and each R is independently H or methyl, or (ii) n is 1 and R is substituted or unsubstituted alkyl, alkenyl, alkynyl, aryl or aralkyl, wherein the substituted alkyl, alkenyl or alkynyl includes at most one heteroatom for every four carbon atoms; and
  (c) each Z subunit is independently alanine, asparagine, cysteine, glutamine, glycine, histidine, lysine, methionine, serine or threonine.

25. The conjugate of claim 24, wherein the arginine-rich peptide has the sequence identified as SEQ ID NO:17.

26. The conjugate of claim 20, wherein the compound comprises a sequence of morpholino subunits, each morpholino subunit comprising a phosphorus-containing linkage connecting the morpholino nitrogen of one morpholino subunit to an exocyclic carbon at the morpholino 3-position of an adjacent morpholino subunit.

27. The conjugate of claim 26, wherein each morpholino subunit comprises a phosphorodiamidate linkage, and each morpholino subunit has independently the following structure:

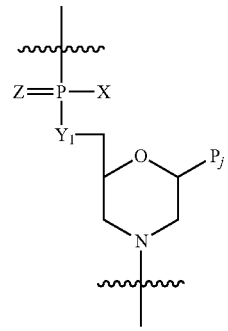

where $Y_1$ is O, Z is O, Pj is a purine or pyrimidine base-pairing moiety—capable of base-specific hydrogen bonding to a base in a polynucleotide; and X is alkyl, alkoxy, thioalkoxy or alkyl amino.

28. The conjugate of claim 20, wherein the conjugate inhibits the synthesis of c-myc in a cellular system, and the compound has the sequence identified as SEQ ID NO: 1, where at least one of the four contiguous guanine (G) bases in SEQ ID NO: 1 is substituted with an inosine (I) base.

29. The method of claim 10, wherein the compound has the sequence identified as SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 10.

30. The method of claim 19, wherein the compound has the sequence identified as SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 10.

31. The conjugate of claim 28, wherein the compound has the sequence identified as SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO: 10.

32. The method of claim 15, wherein the arginine-rich peptide has the sequence identified as SEQ ID NO:16.

33. The conjugate of claim 24, wherein the arginine-rich peptide has the sequence identified as SEQ ID NO:16.

* * * * *